(12) United States Patent
Zhao et al.

(10) Patent No.: US 11,835,527 B2
(45) Date of Patent: Dec. 5, 2023

(54) DEGLYCOSYLATION METHODS FOR ELECTROPHORESIS OF GLYCOSYLATED PROTEINS

(71) Applicant: Regeneron Pharmaceuticals, Inc., Tarrytown, NY (US)

(72) Inventors: Yiming Zhao, Great Neck, NY (US); Hunter Chen, New York, NY (US); Shao-Chun Wang, Briarcliff Manor, NY (US); Timothy Riehlman, East Greenbush, NY (US); Gabriel Carreau, Delmar, NY (US); Ying Wang, Basking Ridge, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 379 days.

(21) Appl. No.: 17/153,150

(22) Filed: Jan. 20, 2021

(65) Prior Publication Data
US 2021/0223256 A1    Jul. 22, 2021

Related U.S. Application Data

(60) Provisional application No. 62/963,646, filed on Jan. 21, 2020.

(51) Int. Cl.
*G01N 27/447* (2006.01)
*G01N 33/58* (2006.01)
(Continued)

(52) U.S. Cl.
CPC ....... *G01N 33/6842* (2013.01); *G01N 27/041* (2013.01); *G01N 27/44791* (2013.01);
(Continued)

(58) Field of Classification Search
CPC .... G01N 27/447; G01N 33/582; G01N 33/68; G01N 2400/00; G01N 2440/38; C07K 1/26
See application file for complete search history.

(56) References Cited

U.S. PATENT DOCUMENTS 4,859,581 A    8/1989 Nicolson et al.
5,610,279 A    3/1997 Brockhaus et al.
(Continued)

FOREIGN PATENT DOCUMENTS

CN    105277398 A    1/2016
EP       2686680 B1    6/2018
(Continued)

OTHER PUBLICATIONS

Ashkenazi et al., "Protection against endotoxic shock by a tumor necrosis factor receptor immunoadhesin," PNAS USA, Dec. 1991, 88:10535-10539.
(Continued)

*Primary Examiner* — Luan V Van
*Assistant Examiner* — Caitlyn Mingyun Sun
(74) *Attorney, Agent, or Firm* — COOLEY LLP; Matthew Pavao; Ivor R. Elrifi

(57) ABSTRACT

The disclosure relates to methods of analyzing a post-translationally modified protein of interest using electrophoresis, the methods comprising deglycosylating the protein of interest after labeling.

31 Claims, 15 Drawing Sheets
(14 of 15 Drawing Sheet(s) Filed in Color)
Specification includes a Sequence Listing.

(51) Int. Cl.
*G01N 33/68* (2006.01)
*G01N 27/04* (2006.01)

(52) U.S. Cl.
CPC ....... *G01N 33/582* (2013.01); *G01N 2440/38* (2013.01); *G01N 2570/00* (2013.01)

(56) References Cited

U.S. PATENT DOCUMENTS

| | | |
|---|---|---|
| 6,924,372 B2 | 8/2005 | Czerney et al. |
| 7,087,411 B2 | 8/2006 | Daly et al. |
| 7,279,159 B2 | 10/2007 | Daly et al. |
| 7,582,298 B2 | 9/2009 | Stevens et al. |
| 7,879,984 B2 | 2/2011 | Martin et al. |
| 8,043,617 B2 | 10/2011 | Stevens et al. |
| 8,062,640 B2 | 11/2011 | Sleeman et al. |
| 8,309,088 B2 | 11/2012 | MacDonald et al. |
| 8,586,713 B2 | 11/2013 | Davis et al. |
| 8,735,095 B2 | 5/2014 | Martin et al. |
| 8,871,209 B2 | 10/2014 | Stitt et al. |
| 8,945,559 B2 | 2/2015 | Dix et al. |
| 9,018,356 B2 | 4/2015 | Sleeman et al. |
| 9,079,948 B2 | 7/2015 | Orengo et al. |
| 9,132,192 B2 | 9/2015 | Daly et al. |
| 9,173,880 B2 | 11/2015 | Dix et al. |
| 9,228,014 B2 | 1/2016 | Classon et al. |
| 9,260,515 B2 | 2/2016 | Stitt et al. |
| 9,265,827 B2 | 2/2016 | Wiegand et al. |
| 9,302,015 B2 | 4/2016 | Papadopoulos et al. |
| 9,353,176 B2 | 5/2016 | MacDonald et al. |
| 9,402,898 B2 | 8/2016 | Walsh et al. |
| 9,447,173 B2 | 9/2016 | Gurnett-Bander et al. |
| 9,453,072 B2 | 9/2016 | Murphy et al. |
| 9,540,449 B2 | 1/2017 | Yancopoulos et al. |
| 9,637,535 B2 | 5/2017 | Murphy et al. |
| 9,657,102 B2 | 5/2017 | Smith et al. |
| 9,664,608 B2 | 5/2017 | Reed et al. |
| 2005/0186641 A1 | 8/2005 | Haugland et al. |
| 2012/0039908 A1 | 2/2012 | Combs et al. |
| 2014/0088295 A1 | 3/2014 | Smith et al. |
| 2014/0271681 A1 | 9/2014 | Martin et al. |
| 2015/0203579 A1 | 7/2015 | Papadopoulos et al. |
| 2015/0203580 A1 | 7/2015 | Papadopoulos et al. |
| 2015/0259423 A1 | 9/2015 | Kirshner et al. |
| 2015/0266966 A1 | 9/2015 | Smith et al. |
| 2015/0313194 A1 | 11/2015 | Hu et al. |
| 2015/0337029 A1 | 11/2015 | Kyratsous et al. |
| 2015/0337045 A1 | 11/2015 | Okamoto et al. |
| 2015/0346194 A1 | 12/2015 | Magnelli et al. |
| 2016/0017029 A1 | 1/2016 | Walsh et al. |
| 2016/0069890 A1 | 3/2016 | Wu et al. |
| 2016/0075778 A1 | 3/2016 | Okamoto et al. |
| 2016/0215040 A1 | 7/2016 | Kyratsous et al. |
| 2016/0348139 A1* | 12/2016 | Kimzey ................. G01N 33/68 |
| 2018/0095084 A1 | 4/2018 | Wu et al. |
| 2018/0299461 A1 | 10/2018 | Cox |
| 2019/0170763 A1* | 6/2019 | Kimzey ............... G01N 33/582 |
| 2019/0285580 A1 | 9/2019 | Riehlman et al. |

FOREIGN PATENT DOCUMENTS

| | | | |
|---|---|---|---|
| JP | 2006038674 A | 2/2006 | |
| WO | WO-2013192530 A2 | 12/2013 | |
| WO | WO 2014/144198 A1 | 9/2014 | |
| WO | WO 2015/184325 A2 | 12/2015 | |
| WO | WO 2016/069764 A1 | 5/2016 | |
| WO | WO-2016069764 A1 * | 5/2016 | ............. C12P 19/28 |
| WO | WO-2018092078 A1 * | 5/2018 | ............... C07K 1/16 |
| WO | WO-2019182901 A1 | 9/2019 | |
| WO | WO-2021150558 A1 | 7/2021 | |

OTHER PUBLICATIONS

Byrn et al., "Biological properties of a CD4 immunoadhesin," Nature (1990) 344:667-670.

Caliper LifeSciences, "Rapid Analysis of N-Glycans on the LabChip GXII Microchip-CE Platform," Application Note 403, LCGX-AP-403, Dec. 2009, 4 pages.

Engel et al., "Challenges of glycoprotein analysis by microchip capillary gel electrophoresis," Electrophoresis, 2015, 36: 1754-1758.

Hollenbaugh et al., "Construction of Immunoglobulin Fusion Proteins," Current Protocols in Immunology (2002), Supplement 48, Unit 10.19A, pp. 10.19A.1-10.19A.11.

Holliger et al., "Diabodies: small bivalent and bispecific antibody fragments," PNAS USA, Jul. 1993, 90:6444-6448.

Kipriyanov et al., "Recombinant single-chain Fv fragments carrying C-terminal cysteine residues: Production of bivalent and biotinylated miniantibodies," Mol. Immunol. (1994) 31:1047-1058.

Kipriyanov et al., "Single-chain antibody streptavidin fusions: tetrameric bifunctional scFv-complexes with biotin binding activity and enhanced affinity to antigen," Human Antibodies and Hybridomas (1995) 6:93-101.

Poljak, RJ, "Production and structure of diabodies," Structure, Dec. 1994, 2:1121-1123.

Taylor et al., "A transgenic mouse that expresses a diversity of human sequence heavy and light chain immunoglobulins," Nucl. Acids Res., (1992) 20(23):6287-6295.

Ward et al., "Binding activities of a repertoire of single immunoglobulin variable domains secreted from *Escherichia coli*," Nature (1989) 341:544-546.

Bryant, S. K., "The development of capillary electrophoresis assays to study enzyme inhibition", Louisiana State University and Agricultural & Mechanical College (2013); 138 pages.

Jensen, P. F., et al., "Removal of N-linked glycosylations at acidic pH by PNGase A facilitates hydrogen/deuterium exchange mass spectrometry analysis of N-linked glycoproteins", Analytical Chemistry (2016); 88(24): 12479-12488.

Lu, G., et al., "Capillary electrophoresis separations of glycans", Chemical Reviews (2018); 118(17): 7867-7885.

* cited by examiner

DEGLYCOSYLATION METHODS FOR ELECTROPHORESIS OF GLYCOSYLATED PROTEINS

CROSS REFERENCE TO RELATED APPLICATIONS

This application claims the benefit of priority to U.S. Provisional patent Application Ser. No. 62/963,646 filed on Jan. 21, 2020, the contents of which are hereby incorporated by reference in their entirety.

TECHNICAL FIELD

The disclosure relates to the fields of biochemistry, molecular biology and the analysis of proteins via electrophoresis.

INCORPORATION BY REFERENCE OF SEQUENCE LISTING

The contents of the text file submitted electronically herewith are incorporated herein by reference in their entirety: A computer readable format copy of the Sequence Listing (filename: REGE-019-001US_SeqList_ST25.txt, date recorded: Jan. 19, 2021, file size 1 kilobyte).

BACKGROUND

Capillary based electrophoresis (CE) and microchip based capillary electrophoresis (MCE) are common analytical methods in the pharmaceutical industry used to characterize therapeutic protein integrity and purity based on protein size, and provide quality control. While standard, industry recommended sample preparation methods work well for many proteins, heavily glycosylated proteins are problematic due to poor separation and quantification by CE and MCE. In addition, partially glycosylated peaks and non-glycosylated peak in the MCE profile may overlap with impurity peaks and interfere with quantification. There thus exists a need in the art for additional sample preparation methods that can overcome the challenges of working with glycosylated proteins. This invention provides methods for labeling heavily glycosylated proteins that can be used to prepare proteins for analysis by electrophoresis methods such as CE and MCE.

SUMMARY

The disclosure provides methods of analyzing a sample comprising a protein of interest, the methods comprising denaturing, fluorescently labeling, quenching and deglycosylating the sample; wherein the denaturing, labeling and quenching steps occur prior to deglycosylation. The methods of analyzing a sample of the disclosure can reduce or eliminate electropherogram peaks due to endoglycosidase, and can reduce free dye interference, thereby providing fast, accurate and highly reproducible and high throughput methods through which glycoproteins can be analyzed.

The disclosure provides methods of analyzing a sample comprising a protein of interest, the methods comprising: (a) denaturing the sample; (b) labeling the sample with a fluorescent label to produce a labeled sample; (c) quenching un-reacted fluorescent label in the labeled sample; (d) deglycosylating the labeled sample with an endoglycosidase; and (e) performing electrophoresis on the labeled sample; wherein the sample is denatured, labeled and quenched in steps (a) through (c) prior to deglycosylation in step (d).

In some embodiments of the methods of the disclosure, the protein of interest comprises at least one glycosylation site. In some embodiments, the protein is of interest is a glycosylated protein. In some embodiments, the glycosylated protein comprises at least one attached glycan. In some embodiments, at least 1%, at least 2%, at least 3%, at least 4%, at least 5% or at least 10% of the total weight of the glycosylated protein comprises glycans (10% w/w).

In some embodiments of the methods of the disclosure, the protein of interest comprises an antigen binding domain. In some embodiments, the protein of interest comprises an antibody, an antibody fragment or an scFv. In some embodiments, the protein of interest comprises an Fc domain. In some embodiments, the protein of interest comprises a receptor fusion protein. In some embodiments, the receptor fusion protein is a receptor-Fc-fusion protein or a soluble TCR-Fc fusion protein. In some embodiments, the receptor fusion protein is a trap protein or a mini trap protein. In some embodiments, the protein of interest is a trap protein or a mini trap protein. In some embodiments, the protein of interest is a recombinant human protein.

In some embodiments of the methods of the disclosure, the glycosylation site comprises an Asn-X-Ser/Thr consensus sequence. In some embodiments, the at least one attached glycan is N-linked. In some embodiments, the at least one attached glycan is N-linked to an asparagine in the glycosylated protein. In some embodiments, the endoglycosidase catalyzes deglycosylation of N-linked glycans. In some embodiments, the endoglycosidase is selected from the group consisting of Peptide-N-Glycosidase F (PNGase F), Endoglycosidase H (Endo H), Endoglycosidase S (Endo S), Endoglycosidase D, Endoglycosidase F1, Endoglycosidase F2 and Endoglycosidase F4. In some embodiments, the endoglycosidase is PNGase F. In some embodiments, the PNGase F is Rapid PNGase F. In some embodiments, the Rapid PNGase F is non-reducing. In some embodiments, the PNGase F is reducing.

In some embodiments of the methods of the disclosure, deglycosylating the sample comprises heating the sample to about 35° C. for 30 minutes. In some embodiments, deglycosylating the sample comprises heating the sample to about 50° C. for between 10 and 30 minutes. In some embodiments, deglycosylating the sample comprises heating the sample to about 50° C. for 10 minutes. In some embodiments, deglycosylating the sample comprises a reaction mixture comprising between 0.2-1.5 mg labeled protein of interest, and between 1-5 µL Rapid PNGase F in a 10 µL reaction volume, excluding the volume of the Rapid PNGase F. In some embodiments, the reaction mixture comprises 0.2 mg labeled protein of interest. In some embodiments, the reaction mixture comprises 5 µL Rapid PNGase F. In some embodiments, the reaction mixture comprises a buffer.

In some embodiments of the methods of the disclosure, the at least one glycan is an O-linked glycan. In some embodiments, the endoglycosidase catalyzes deglycosylation of O-linked glycans. In some embodiments, the endoglycosidase comprises Endo-α-N-acetylgalactosamindase (O-glycosidase).

In some embodiments of the methods of the disclosure, labeling the sample with the fluorescent label comprises heating the sample to about 35° C. for 10-30 minutes. In some embodiments, labeling the sample with the fluorescent label comprises heating the sample to about 35° C. for 15 minutes.

In some embodiments of the methods of the disclosure, the sample is denatured using a reducing solution. In some embodiments, the reducing solution comprises dithiothreitol (DTT). In some embodiments, the sample is denatured using a non-reducing solution. In some embodiments, the non-reducing solution comprises iodoacetamide (IAM). In some embodiments, denaturing the sample comprises heating the sample to between 40° C. and 99° C. for between 1 minute and 5 hours. In some embodiments, denaturing the sample comprises heating the sample to between 50° C. and 99° C. for between 1 to 60 minutes.

In some embodiments of the methods of the disclosure, quenching the un-reacted fluorescent label comprises adding a stop solution.

In some embodiments of the methods of the disclosure, the methods further comprise analyzing a reference standard in parallel to the sample.

In some embodiments of the methods of the disclosure, the electrophoresis is selected from the group consisting of gel electrophoresis, isoelectric focusing, capillary electrophoresis (CE) or microchip capillary electrophoresis (MCE). In some embodiments, the electrophoresis is MCE. In some embodiments, the MCE is carried out using an MCE instrument.

In some embodiments of the methods of the disclosure, methods result in reduced free dye interference in the less than 20 kDa range and a reduced or absent endoglycosidase peak in an electropherogram when compared to an electropherogram generated using a sample labeled after deglycosylation. In some embodiments, the endoglycosidase peak is reduced by at least 5%, at least 10%, at least 20%, at least 30%, at least 40%, at least 50%, at least 60%, at least 70%, at least 80% or at least 90% when compared to an electropherogram generated using a sample labeled after deglycosylation. In some embodiments, the endoglycosidase peak is absent in an electropherogram when compared to an electropherogram generated using a sample labeled after deglycosylation.

The disclosure provides methods of determining stability of a protein of interest comprising: (a) stressing a sample comprising the protein of interest; (b) denaturing the stressed sample and a non-stressed sample comprising the protein of interest; (c) labeling the stressed sample and the non-stressed sample with a fluorescent label to produce a labeled stressed sample and a labeled non-stressed sample; (d) quenching un-reacted fluorescent label in the labeled stressed sample and the labeled non-stressed sample; (e) deglycosylating the labeled stressed sample and the labeled non-stressed sample with an endoglycosidase; (f) performing microchip capillary electrophoresis (MCE) on the labeled stressed sample and the labeled non-stressed sample to generate electropherograms for the stressed sample and the non-stressed sample; and (g) comparing the electropherograms from the stressed sample and the nonstressed sample, thereby determining the stability of the protein of interest; wherein the stressed sample and the non-stressed sample are denatured, labeled and quenched in steps (b) through (d) prior to deglycoslation in step (e).

In some embodiments of the methods of the disclosure, stressing the sample comprises thermally stressing the sample. In some embodiments, thermally stressing the sample comprises holding the sample at between about 30° C. and about 45° C. for at least 1 week, at least 2 weeks, at least 3 weeks, at least 4 weeks, at least 5 weeks, at least 6 weeks, at least 7 weeks or at least 8 weeks.

In some embodiments of the methods of the disclosure, stressing the sample comprises at least one freeze/thaw cycle.

In some embodiments of the methods of the disclosure, stressing the sample comprises exposing the sample to storage conditions. In some embodiments, the storage conditions comprise a temperature of about −80° C. to −30° C. for at least 1 week, at least 2 weeks, at least 3 weeks, at least 1 month, at least 2 months, at least 3 months, at least 6 months, at least 8 months, at least 12 months, at least 18 months, at least 24 months or at least 30 months. In some embodiments, the storage conditions comprise a temperature of about 2° C. to 8° C. for at least 1 week, at least 2 weeks, at least 3 weeks, at least 1 month, at least 2 months, at least 3 months, at least 6 months, at least 8 months, at least 12 months or at least 18 months.

In some embodiments of the methods of the disclosure, stressing the sample comprises mechanically agitating the sample.

In some embodiments of the methods of the disclosure, stressing the sample comprises lyophilizing and rehydrating the sample.

In some embodiments of the methods of the disclosure, stressing the sample comprises exposing the sample to light, radiation, singlet oxygen species, free radicals, high pH conditions or low pH conditions.

In some embodiments of the methods of the disclosure, the protein of interest comprises at least one glycosylation site. In some embodiments, the protein is of interest is a glycosylated protein. In some embodiments, the glycosylated protein comprises at least one attached glycan. In some embodiments, at least 1%, at least 2%, at least 3%, at least 4%, at least 5% or at least 10% of the total weight of the glycosylated protein comprises glycans (10% w/w). In some embodiments, at least 10% of the total weight of the glycosylated protein comprises glycans (10% w/w).

In some embodiments of the methods of the disclosure, the protein of interest comprises an antigen binding domain. In some embodiments, the protein of interest comprises an antibody, an antibody fragment or an scFv. In some embodiments, the protein of interest comprises an Fc domain. In some embodiments, the protein of interest comprises a receptor fusion protein. In some embodiments, the receptor fusion protein is a receptor-Fc-fusion protein or a soluble TCR-Fc fusion protein. In some embodiments, the receptor fusion protein is a trap protein or a mini trap protein. In some embodiments, the protein of interest is a trap protein or a mini trap protein. In some embodiments, the protein of interest is a recombinant human protein.

In some embodiments of the methods of the disclosure, the glycosylation site comprises an Asn-X-Ser/Thr consensus sequence. In some embodiments, the at least one attached glycan is N-linked. In some embodiments, the at least one attached glycan is N-linked to an asparagine in the glycosylated protein. In some embodiments, the endoglycosidase catalyzes deglycosylation of N-linked glycans. In some embodiments, the endoglycosidase is selected from the group consisting of Peptide-N-Glycosidase F (PNGase F), Endoglycosidase H (Endo H), Endoglycosidase S (Endo S), Endoglycosidase D, Endoglycosidase F1, Endoglycosidase F2 and Endoglycosidase F4. In some embodiments, the endoglycosidase is PNGase F. In some embodiments, the PNGase F is Rapid PNGase F. In some embodiments, the Rapid PNGase F is non-reducing. In some embodiments, the Rapid PNGase F is reducing.

In some embodiments of the methods of the disclosure, deglycosylating the stressed and non-stressed samples comprises heating the samples to about 35° C. for 30 minutes. In some embodiments, deglycosylating the stressed and non-stressed samples comprises heating the samples to about 50° C. for between 10 and 30 minutes. In some embodiments, deglycosylating the stressed and non-stressed samples comprises heating the samples to about 50° C. for 10 minutes. In some embodiments, deglycosylating the stressed and non-stressed samples comprises a reaction mixture for each sample comprising between 0.2-1.5 mg labeled protein of interest, and between 1-5 µL Rapid PNGase F in a 10 µL reaction volume excluding the volume of the Rapid PNGase F. In some embodiments, the reaction mixture for each of the stressed and non-stressed samples comprises 5 µL Rapid PNGase F. In some embodiments, each of the stressed and non-stressed sample comprise 0.2 mg labeled protein of interest. In some embodiments, the reaction mixture for each of the stressed and non-stressed samples comprises a buffer.

In some embodiments of the methods of the disclosure, the at least one glycan is an O-linked glycan. In some embodiments, the endoglycosidase catalyzes deglycosylation of O-linked glycans. In some embodiments, the endoglycosidase comprises Endo-α-N-acetylgalactosamindase (O-glycosidase).

In some embodiments of the methods of the disclosure, labeling the stressed and non-stressed samples with the fluorescent label comprises heating each sample to about 35° C. for 30 minutes.

In some embodiments of the methods of the disclosure, the stressed and non-stressed samples are denatured using a reducing solution. In some embodiments, the reducing solution comprises dithiothreitol (DTT). In some embodiments, the stressed and non-stressed samples are denatured using a non-reducing solution. In some embodiments, the non-reducing solution comprises iodoacetamide (IAM). In some embodiments, denaturing the stressed and non-stressed samples comprises heating the samples to between 40° C. and 99° C. for between 1 minute and 5 hours. In some embodiments, denaturing the stressed and non-stressed samples comprises heating the samples to between 50° C. and 99° C. for between 1 to 60 minutes.

In some embodiments of the methods of the disclosure, quenching the un-reacted fluorescent label comprises adding a stop solution.

In some embodiments of the methods of the disclosure, the methods further comprise analyzing a reference standard in parallel to the stressed and non-stressed samples. In some embodiments, comparing the electropherograms for the stressed and non-stressed samples comprises comparing peak number, height, position, area, or a combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
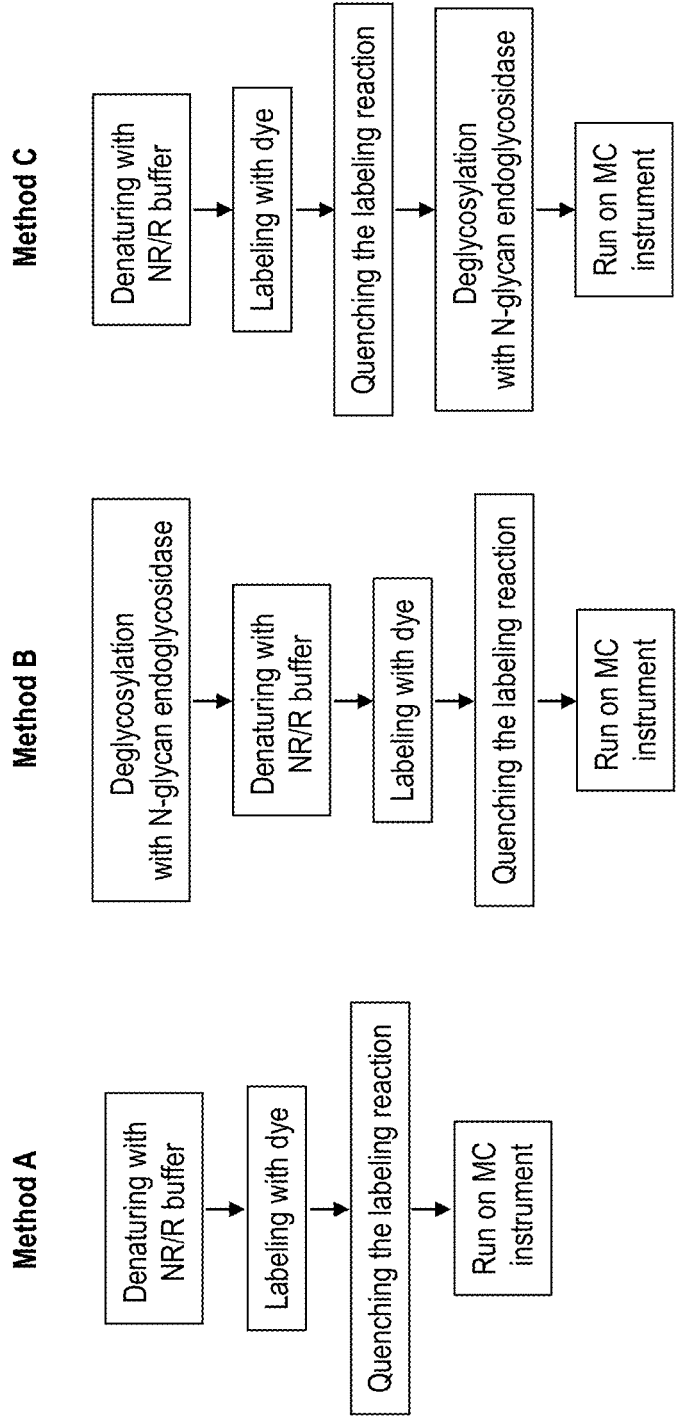
FIG. 1 is a diagram showing protocols for Method A, without deglycosylation; Method B, deglycosylation prior to labeling; and Method C, deglycosylation after labeling. NR: non-reducing, R: reducing, MC: microchip capillary electrophoresis.

The present disclosure provides new methods for preparing a sample comprising a protein of interest for analysis via electrophoresis. In the methods provided herein, the protein of interest is denatured, followed by covalent labeling of the protein using a fluorescent dye, and subsequently quenching the labeling reaction. Following labeling, the labeled protein is contacted with an enzyme such as an endoglycosidase to remove glycans from the protein of interest without further purification. Unlike previous methods of preparing glycosylated proteins for electrophoresis, which deglycosylate the proteins prior to labeling, the methods described herein allow for clear separation of protein and peptide species based on mass. These methods also eliminate interference from the enzyme used in deglycosylation, and free dye from the labeling reaction, in microchip electrophoresis (MCE) electropherograms. The methods are fast, highly reproducible and high throughput, and have been successfully used to analyze glycosylated proteins. Without wishing to be bound by theory, it is thought that the methods described herein are advantageous with respect to heavily glycosylated proteins, as heavy glycosylation interferes with migration of the protein in the MCE or capillary electrophoresis (CE) analysis platforms, resulting in incorrect measurements of protein molecular weight and imprecise electropherogram peaks. The methods describe herein can be used in a platform approach which is applicable to any glycosylated proteins analyzed by methods such as CE and MCE, and to characterize the proteins or for quality control purposes. For example, the methods described herein can be used to measure the stability of a protein of interest when subjected to various conditions, such prolonged holding times at various temperatures, or different formulations.

Accordingly, the disclosure provides methods of preparing a sample comprising a protein of interest for analysis using electrophoresis, comprising (a) denaturing the sample; (b) labeling the sample with a fluorescent label to produce a labeled sample; (c) quenching un-reacted fluorescent label in the labeled sample; (d) deglycosylating the labeled sample with an endoglycosidase; and (e) performing electrophoresis on the labeled sample; wherein the sample is labeled and quenched in steps (b) and (c) prior to deglycosylation in step (d). In some embodiments, the electrophoresis is microchip capillary electrophoresis (MCE), and the output is an electropherogram.

Definitions

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied.

As used herein, "protein" refers to a molecule comprising two or more amino acid residues joined to each other by a peptide bond. Proteins include polypeptides and peptides, and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by genetic engineering techniques (e.g., such as a sequence encoding a chimeric protein, or a codon-optimized sequence, an intronless sequence, etc.) where it may reside as an episome or be integrated into the genome of the cell.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications, patents, and patent applications mentioned in this specification are herein incorporated by reference to the same extent as if each individual publication, patent, or patent application was specifically and individually indicated to be incorporated by reference.

Denaturing

The disclosure provides methods of denaturing a protein of interest in a sample. Denaturing proteins involves the disruption of secondary and tertiary protein structures under conditions insufficient to disrupt peptide bonds, leaving the primary structure intact.

Methods of denaturing a protein of interest under both reducing and non-reducing conditions are within the scope of the disclosure.

A protein reducing agent is an agent that disrupts disulfide bonds. These disulfide bonds can be within a single polypeptide, or between multiple subunits of a protein encoded on separate polypeptide. Disrupting disulfide bonds between subunits allows for the analysis of the individual subunits of a multi-subunit protein to be analyzed individually. Reducing agents will be known to persons of ordinary skill in the art. Exemplary reducing agents include. but are not limited to, dithiothreitol (DTT, CAS 3483-12-3), beta-mercaptoethanol (BME, 2BME, 2-ME, b-mer, CAS 60-24-2), 2-aminoethanethiol (2-MEA-HCl, also called cysteamine-HCl, CAS 156-57-0), Tris (2-carboxyethyl) phosphine hydrochloride, (TCEP, CAS 5961-85-3), cysteine hydrochloride (Cys-HCl, CAS 52-89-1), or 2-mercaptoethanesulfonic acid sodium salt (MESNA). Other methods for reducing protein bonds are known in the art, such as an immobilized reductant column which contains resin to which a thiol-based reducing agent has been immobilized to enable the solid-phase reduction of peptide and protein disulfide bonds. Reducing agents, including oxidizing agents, are suitable for reducing chemical interaction between polypeptides are also envisioned.

In some embodiments, the protein of interest is denatured using a reducing solution. In some embodiments, the reducing solution contains 135 to 155 mM dithiothreitol (DTT). In some embodiments, the reducing solution further comprises sodium phosphate and lithium dodecyl sulfate. In some embodiments, the reducing solution comprises or consists essentially of 0.69% lithium dodecyl sulfate (LDS), 69 mM sodium phosphate, and 142 mM dithiothreitol. In some embodiments, the reducing solution contains 40-120 mM DTT, 40-80 mM sodium phosphate and 0.5% to 2.0% LDS. In some embodiments, the reducing solution contains 60-100 mM DTT, 50-70 mM sodium phosphate and 0.75% to 1.5% LDS. In some embodiments, the reducing solution contains about 80 mM DTT, about 60 mM sodium phosphate and about 1.2% LDS. In some embodiments, the reducing solution is added to the sample comprising the protein of interest at a ratio of about 1:4 by volume.

In some embodiments, the protein of interest is denatured using a non-reducing solution, i.e. under conditions which preserve disulfide bonds in the protein of interest. In some embodiments, the non-reducing solution comprises iodoacetamide (IAM). In some embodiments, the non-reducing solution comprises between 100 and 200 mM iodoacetamide. In some embodiments, the non-reducing solution further comprises sodium phosphate and lithium dodecyl sulfate (LDS). In some embodiments, the non-reducing solution comprises 166 mM iodoacetamide (IAM). In some embodiments, the non-reducing solution comprises, or consists essentially of, 166 mM iodoacetamide, 0.81% lithium dodecyl sulfate and 81 mM sodium phosphate. In some embodiments, the non-reducing solution comprises 100-300 mM iodoacetamide, 40-80 mM sodium phosphate, and 0.5% to 2.0% LDS. In some embodiments, the non-reducing solution comprises, 150-250 mM iodoacetamide, 50-70 mM sodium phosphate, and 0.75% to 1.5% LDS. In some embodiments, the non-reducing solution comprises about 200 mM iodoacetamide, about 60 mM sodium phosphate, and about 1.2% LDS. In some embodiments, the non-reducing solution is added to the sample comprising the protein of interest at a ratio of about 1:4 by volume.

In some embodiments, denaturing the sample comprises adding a reducing or non-reducing solution to the sample, and heating the combined sample and reducing or non-reducing solution. In some embodiments, the sample is denatured by heat. For example, the combined sample and reducing or non-reducing solution can be heated to between 30° C. and 99° C., between 30° C. and 90° C., between 30° C. and 80° C., between 30° C. and 70° C., between 30° C. and 60° C., between 30° C. and 50° C., between 30° C. and 40° C., between 40° C. and 99° C., between 40° C. and 90° C., between 40° C. and 80° C., between 40° C. and 70° C., between 40° C. and 60° C., between 40° C. and 50° C., between 50° C. and 99° C., between 50° C. and 90° C., between 50° C. and 80° C., between 50° C. and 70° C., or between 50° C. and 60° C. In some embodiments, the combined sample and reducing or non-reducing solution can be heated for between 1 minute and 12 hours, between 1 minute and 10 hours, between 1 minute and 5 hours, between 1 minute and 4 hours, between 1 minute and 3 hours, between 1 minute and 2 hours, between 1 minute and 60 minutes, between 1 minute and 30 minutes, between 1 minute and 15 minutes, between 1 minute and 10 minutes, between 1 minute and 5 minutes, between 5 minute and 60 minutes, between 5 minutes and 30 minutes, between 5 minute and 15 minutes, between 5 minute and 10 minutes, between 10 minute and 60 minutes, between 10 and 45 minutes, between 10 minutes and 30 minutes, or between 10 minutes and 15 minutes. In some embodiments, the combined sample and reducing or non-reducing solution can be heated to between 40° C. and 99° C. for between 1 minute and 60 minutes. In some embodiments, the combined sample and reducing or non-reducing solution can be heated to between 50° C. and 99° C. for between 1 minute and 60 minutes. As a further example, the combined sample and reducing or non-reducing solution can be heated to between 60° C. and 85° C. for between 5 to 30 minutes. Alternatively, the combined sample and reducing or non-reducing solution can be heated to 75° C. for 10 minutes. In some embodiments, the combined sample and reducing or non-reducing solution is heated to 70° C. for 10 minutes.

Deglycosylation

The disclosure provides methods of deglycosylating a protein of interest in a sample. In some embodiments, the protein of interest is deglycosylated after being labeled with a fluorescent label using the methods described herein. Deglycosylation can be performed using an enzyme such as an endoglycosidase.

Glycoproteins are proteins which contain oligosaccharide chains (glycans) covalently attached to amino acid side-chains. These oligosaccharide chains are attached to the protein in a cotranslational or posttranslational modification.

As used herein, the term "glycan" sometimes used interchangeably with "polysaccharide" and "oligosaccharide" refers to a compound comprising or consisting of glycosidically linked monosaccharides. The term glycan can also be used to refer to a carbohydrate linked to a glycoprotein or glycolipid, even if the carbohydrate is a monosaccharide. Glycans may comprise O-glycosidic linkages of monosaccharides. Glycans can be homo- or heteropolymers of monosaccharides, and can be linear or branched. Exemplary glycans can comprise monomers of mannose, N-Acetylglucosamine (GlcNAc), N-Glycolylneuraminic acid (Neu5Gc), galactose, sialic acid, and fucose, among others.

Glycans can be linked to a protein of interest via either N-linkages or O-linkages, and a protein of interest can comprise N-linked glycans, O-linked glycans or a combination of N-linked and O-linked glycans. As referred to herein, "N-linked glycans" or "N-linked glycosylation" refers to the attachment of a sugar monomer or polysaccharide to a nitrogen atom such as the amide nitrogen of an asparagine (Asn) amino acid of a protein. As used herein, "O-linked glycans" or "O-linked glycosylation" refers to the attachment of a sugar monomer or polysaccharide to the oxygen atom of a serine (Ser) or threonine (Thr) amino acid of a protein. Exemplary O-linked glycans include, but are not limited to, O—N-acetylgalactosamine (O-GalNAc), O—N-acetylglucosamine (O-GlcNAc), O-Mannose, O-Galactose, O-Fucose and O-Glucose.

Endoglycosidases are enzymes that that hydrolyze internal glycosidic bonds in oligosaccharides. When the oligosaccharides are part of a glycoprotein, the oligosaccharides are released from the glycoprotein thereby.

As used herein, an "endoglycosidase" refers to an enzyme that releases glycans from glycoproteins or glycolipids. Endoglycosidases may cleave polysaccharide changes between residues that are not the terminal residue, and are thus capable of releasing long chain carbohydrates from their cognate protein conjugates. Exemplary endoglycosidases include, but are not limited to, Peptide-N-Glycosidase F (PNGase F), Endoglycosidase H (Endo H), Endoglycosidase S (Endo S). Endoglycosidase D, Endoglycosidease F1, Endoglycosidase F2, Endoglycosidase F3, O-glycosidase and Endo-β-Galactosidase.

In some embodiments, the endoglycosidase catalyzes the deglycosylation of N-linked glycans. Exemplary endoglycosidases that target N-linked glycans include, but are not limited to, Peptide-N-Glycosidase F (PNGase F), Endoglycosidase H (Endo H), Endoglycosidase S (Endo S), Endoglycosidase D, Endoglycosidase F1, Endoglycosidase F2 and Endoglycosidase F4. In some embodiments, for example those embodiments wherein the protein of interest comprises N-linked glycans, the endoglycosidase is PNGase F.

In some embodiments, the endoglycosidase catalyzes the deglycosylation of O-linked glycans. Exemplary endoglycosidases that target O-linked glycans include, but are not limited to, Endo-α-N-Acetylgalactosaminidase (O-glycosidase).

In some embodiments, the endoglycosidase is PNGAse F. PNGase F is an amidase that cleaves between the innermost N-Acetyl-D-Glucosamine (GlcNAc) and asparagine residues of high mannose, hybrid and complex oligosaccharides in N-linked glycoproteins. In some embodiments, the PNGase F is recombinant. In some embodiments, the PNGase F is Rapid™ PNGAse F. Rapid™ PNGase F is known in the art and is available from New England Biolabs and other vendors. In some embodiments, the Rapid™ PNGase F is in a non-reducing format that preserves disulfide bonds in the protein of interest. In some embodiments, the Rapid™ PNGase F is in a reducing format that does not preserve disulfide bonds in the protein of interest.

In some embodiments, deglycosylating the sample comprises a reaction mixture comprising between 0.1 and 3.0 mg labeled protein of interest. In some embodiments, the reaction mixture comprises between 0.1 and 2.0 mg labeled protein of interest. In some embodiments, the reaction mixture comprises between 0.1 and 1.5 mg protein of interest. In some embodiments, the reaction mixture comprises between 0.5 and 1.5 mg protein of interest. In some embodiments, the reaction mixture comprises 0.2 mg labeled protein of interest. In some embodiments, the reaction mixture comprises between 1 and 7 μL of Rapid™ PNGase F enzyme in a 10 μL reaction volume, excluding the volume of the enzyme. In some embodiments, the reaction mixture comprises between 1 and 5 μL of Rapid™ PNGase F enzyme in a 10 μL reaction volume, excluding the volume of the enzyme. In some embodiments, the reaction mixture comprises 1 μL, 2 μL, 3 μL, 4 μL, 5 μL, 6 μL or 7 μL of Rapid™ PNGase F enzyme added to a 10 μL volume comprising the labeled protein of interest. In some embodiments, the reaction mixture comprises 5 μL of Rapid™ PNGase F enzyme in a 10 μL reaction volume, excluding the volume of the enzyme. In some embodiments, the reaction mixture comprises 5 μL Rapid™ PNGase F enzyme added to a 10 μL volume comprising the labeled protein of interest. In some embodiments, the reaction mixture comprises an additional buffer, for example a reaction buffer that facilitates the action of the PNGase F enzyme. In some embodiments, the reaction mixture does not comprise an additional buffer.

In some embodiments, for example those embodiments where the endoglycosidase is PNGase F, deglycosylating the sample comprises heating the sample to 25° C. to 65° C. for between 100 and 60 minutes. In some embodiments, deglycosylating the sample comprises heating the sample to 30° C. to 50° C. for between 20 and 40 minutes. In some embodiments, deglycosylating the sample comprises heating the sample to 35° C. for 30 minutes.

In some embodiments, for example those embodiments where the endoglycosidase is Rapid™ PNGase F, deglycosylating the sample comprises heating the sample 50° C. for between 10 and 30 minutes. In some embodiments, deglycosylating the sample comprises heating the sample 50° C. for 10 minutes.

Protein Labeling

The disclosure provides methods of labeling proteins of interest. In some embodiments, the proteins of interest are labeled prior to deglycosylation. In some embodiments, proteins of interest are labeled with a fluorescent label, such as a fluorescent dye. Any suitable label is envisaged as within the scope of the disclosure.

As used herein, "detectable label" or "label" refers to a chemical used to facilitate identification and/or quantitation of a target substance, such as a protein of interest. Illustrative labels include labels that can be directly observed or measured or indirectly observed or measured. Such labels include, but are not limited to, radiolabels that can be measured with radiation-counting devices; pigments, dyes or other chromogens that can be visually observed or measured with a spectrophotometer; chemiluminescent labels that can be measured by a photomultiplier-based instrument or photographic film, spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems. The label can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate or a spontaneously chemiluminescent product from a suitable precursor. The term label can also refer to a "tag" or hapten that can bind selectively to a labeled molecule such that the labeled molecule, when added subsequently, is used to generate a detectable signal.

Numerous labels are known by those of skill in the art and include, but are not limited to, microparticles, fluorescent dyes, haptens, enzymes and their chromogenic, fluorogenic and chemiluminescent substrates and other labels that are described in the Molecular Probes Handbook Of Fluorescent Probes And Research Chemicals by Richard P. Haugland, 6th Ed., (1996), and its subsequent 7th edition and 8th edition updates issued on CD Rom in November 1999 and May 2001, respectively, the contents of which are incorporated by reference, and in other published sources.

Exemplary fluorescent labels include, but are not limited to fluorescent dyes. As used herein, "fluorescent dye refers to non-protein molecules that absorb light and emit it at a longer wavelength. Exemplary fluorescent dyes include, but are not limited to Alexa Fluor® dyes, fluorescein iso-thiocyanate (FITC), tetramethyl rhodamine iso-thiocyanate (TRITC), DyLight fluors, Cy dyes, IRDyes, HiLyte dyes, sulfonated and/or pegylated coumarin dyes, sulfonated and/or pegylated xanthenes dyes, sulfonated or/pegylated cyanine dyes, and a sulfonated and/or pegylated pyrene dyes.

An additional detectable label includes, but is not limited to Dyomics DY-631 NHS Ester. Other detectable labels that can be used include other dyes, fluorophores, chromophores, mass tags, quantum dots and the like, and those disclosed in U.S. Pat. No. 6,924,372, which is incorporated by reference in its entirety.

Exemplary fluorescent labels also include, but are not limited to, biological fluorophores such as green fluorescent protein, and nanoscale crystals such as quantum dots.

A further exemplary fluorescent label is available from Perkin Elmer as part of the Pico Protein Reagent Kit (also referred to as the Protein Pico Assay Reagent Kit, part number 760498). In some embodiments, the fluorescent label comprises the Perkin Elmer Pico labeling dye. In some embodiments, labeling the protein of interest comprises adding a 4-20 µM Pico dye solution to a sample comprising a protein of interest at a ratio of about 1:1 by volume. In some embodiments, labeling the protein of interest comprises adding a 4 µM, 5 µM, 6 µM, 10 µM, 12 µM, 14 µM, 15 µM, 16 µM, 18 µM, 20 µM or 25 µM Pico dye solution to a sample comprising a protein of interest. In some embodiments, the Pico dye solution is added to the sample comprising the protein of interest at a ratio of about 1:5 dye to sample by volume, 1:4 dye to sample by volume, 1:3 dye to sample by volume, 1:2 dye to sample by volume 1:1 by volume, 2:1 dye to sample by volume, 3:1 dye to sample by volume, 4:1 dye to sample by volume, or 5:1 dye to sample by volume. In some embodiments, labeling the protein of interest comprises adding a 16 µM Pico dye solution to a sample comprising a protein of interest at a ratio of about 1:1 by volume. In some embodiments, the methods comprise and heating the sample and dye.

In some embodiments, the fluorescent label, or dye, is covalently attached to the protein of interest. In some embodiments, the fluorescent label comprises an amine-reactive group, and is covalently attached to free amines in the protein of interest. In some embodiments, the label is non-covalently attached to the protein of interest through a high-affinity interaction.

Additional suitable kits for protein labeling will be known to persons of ordinary skill in the art. Exemplary kits include, but are not limited to, the Antibody/Protein Labeling Kit-FITC from MedChemExpress, and the (Fast) Alexa Fluor® Conjugation Kits.

Any covalently attached fluorescent label, and any methods of attaching the fluorescent label are envisaged as within the scope of the instant methods.

In some embodiments, the sample and the dye are heated to between about 30° C. and 40° C. for about 5 to 40 minutes. In some embodiments, the sample and the dye are heated to between about 30° C. and 40° C. for about 5 minutes, about 10 minutes, about 15 minutes, about 20 minutes, about 25 minutes, about 30 minutes, about 35 minutes or about 40 minutes. In some embodiments, the sample and the dye are heated to about 35° C. for about 5 minutes, about 10 minutes, about 15 minutes, about 20 minutes, about 25 minutes, about 30 minutes, about 35 minutes or about 40 minutes. In some embodiments, the sample and the label are heated to about 35° C. for about 15 minutes. This heating step can produce a sample comprising a denatured, labeled protein of interest. Excess label can optionally be removed from the sample, for example by using a spin filter.

In some embodiments, the labeling reaction is stopped prior to the deglycosylation reaction (quenching). For example, in those embodiments where the fluorescent label is the Perkin Elmer Pico labeling dye, the labeling reaction can be stopped by adding an equal volume of Perkin Elmer Pico stop buffer to the labeling reaction. In some embodiments the labeling reaction is quenched by adding, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL or 20 µL of an appropriate stop solution to the labeling reaction. In some embodiments, the dye is a Perkin Elmer Pico labeling dye, and the labeling reaction is quenched by adding 5 µL of Perkin Elmer Pico stop solution to the labeling reaction. Further exemplary stop buffers, for example when the label comprises an amine-reactive fluorescent dye, include 1.5 M hydroxylamine, pH 8.5. The person of ordinary skill will be able to select an appropriate stop buffer for various dye labeling reactions. Without wishing to be bound by theory, it is thought that quenching the labeling reaction prevents labeling of the endoglycosidase enzyme used for subsequent deglycosylation steps. This prevents or reduces a labeled endoglycosidase peak in the electropherogram used to visualize the labeled sample.

Protein of Interest

The disclosure provides methods of preparing a sample comprising a protein of interest for analysis using electrophoresis. In some embodiments, the protein of interest is glycosylated. In some embodiments, the methods comprise labeling the protein of interest, followed by deglycosylation.

All proteins of interest comprising post-translational modifications such as N-linked or O-linked glycosylation are envisaged as within the scope of the disclosure. In some embodiments, the protein of interest is a therapeutic protein, such as a therapeutic antibody, which can be a drug substance, a formulated drug substance or a drug product.

In some embodiments, the protein of interest comprises an antigen binding domain. In some embodiments, the protein of interest is a fusion protein. In some embodiments, the protein of interest comprises antibody, an antibody fragment or a single chain-variable fragment (scFv). In some embodiments, the protein of interest is an antibody, an antibody fragment or an scFv.

In some embodiments, the protein of interest comprises a recombinant human protein. For example, the protein of interest can comprise a human antibody or antibody fragment, or a humanized antibody or antibody fragment.

As used herein "antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in U.S. Pat. No. 8,586,713, which is incorporated by reference into this application.

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) PNAS USA 90:6444-6448; Poljak et al. (1994) Structure 2:1 121-1 123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31: 1047-1058). Antibody portions, such as Fab and F(ab')2 fragments, can be prepared from whole antibodies using conventional techniques, such as via papain or pepsin digestion of whole antibodies. Moreover, antibodies, antibody portions and immunoadhesion molecules can be obtained using standard recombinant DNA techniques commonly known in the art (see Sambrook et al., 1989).

The term "human antibody" includes antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3.

The term "humanized antibody", as used herein, includes antibodies in which CDR sequences derived from the germline of another mammalian species, such as a mouse, have been grafted onto human framework sequences, or otherwise modified to increase their similarity to antibody variants produced naturally in humans.

In some embodiments, the protein of interest is an antibody. In some embodiments, the antibody is selected from the group consisting of an anti-Programmed Cell Death 1 antibody (e.g. an anti-PD1 antibody as described in U.S. Pat. Appln. Pub. No. US2015/0203579A1), an anti-Programmed Cell Death Ligand-1 (e.g., an anti-PD-L1 antibody as described in in U.S. Pat. Appln. Pub. No. US2015/0203580A1), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPtl3 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-C5 antibody as described in U.S. Pat. Appln. Pub. No US2015/0313194A1), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g., an anti-PCSK9 antibody as described in U.S. Pat. No. 8,062,640 or 9,540,449), an Anti-Growth and Differentiation Factor-8 antibody (e.g. an anti-GDF8 antibody, also known as anti-myostatin antibody, as described in U.S. Pat. No. 8,871,209 or 9,260,515), an anti-Glucagon Receptor (e.g. anti-GCGR antibody as described in U.S. Pat. Appln. Pub. Nos. US2015/0337045A1 or US2016/0075778A1), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat. No. 8,735,095 or 8,945,559), an anti-interleukin 6 receptor antibody (e.g., an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. No. 9,453,072 or 9,637,535), an anti-Respiratory syncytial virus antibody (e.g., anti-RSV antibody as described in U.S. Pat. No. 9,447,173), an anti-Cluster of differentiation 3 (e.g., an anti-CD3 antibody, as described in U.S. Pat. Nos. 9,447,173 and 9,447,173, and in U.S. Application No. 62/222,605), an anti-Cluster of differentiation 20 (e.g., an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in U.S. Pat. Appln. Pub. No. US2015/0337029A1), an anti-Ebola virus antibody (e.g. as described in U.S. Pat. Appln. Pub. No. US2016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g. an anti-NGF antibody as described in U.S. Pat. Appln. Pub. No. US2016/0017029 and U.S. Pat. Nos. 8,309,088 and 9,353,176) and an anti-Protein Y antibody. In some embodiments, the bispecific antibody is selected from the group consisting of an anti-CD3× anti-CD20 bispecific antibody (as described in U.S. Pat. Appln. Pub. Nos. US2014/0088295A1 and US20150266966A1), an anti-CD3× anti-Mucin 16 bispecific antibody (e.g., an anti-CD3× anti-Muc16 bispecific antibody), and an anti-CD3× anti-Prostate-specific membrane antigen bispecific antibody (e.g., an anti-CD3× anti-PSMA bispecific antibody).

In some embodiments, the protein of interest is selected from the group consisting of abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

Proteins of interest can be created or isolated by any means known in the art. These include recombinant means, such as proteins (e.g. antibodies) expressed using a recombinant expression vector transfected into a host cell. Antibodies that are proteins of interest can be isolated from a recombinant, combinatorial human antibody library, isolated from an animal (e.g., a mouse) that is transgenic for human immunoglobulin genes (see e.g., Taylor et al. (1992) Nucl. Acids Res. 20:6287-6295) or prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In some embodiments, the protein of interest comprises an fragment crystallizable (Fc) domain. For example, the protein of interest can be a receptor-Fc-fusion protein or a soluble TCR-Fc fusion protein. In some embodiments, the receptor-Fc-fusion protein is a trap protein.

Fusion proteins comprise two or more parts of the protein which are not otherwise found together in nature. For example, an "Fc fusion protein" can comprise an Fc portion of an immunoglobulin molecule, which is fused to another heterologous domain, such as a receptor ligand binding domain. Preparation of fusion proteins comprising heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a one or more ligand(s). For example, an Fc-fusion protein is a trap, such as for example an interleukin 1 (IL-1) trap (e.g., rilonacept, which contains the IL-1 RAcP ligand binding region fused to the IL-1 R1 extracellular region fused to Fc of hIgG1; see U.S. Pat. No. 6,927,004), or a vascular endothelial growth factor A (VEGF) trap (e.g., aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

In some embodiments, the protein of interest is a fusion protein, such as a receptor fusion protein. Receptor fusion proteins can include, intera alia, trap proteins and mini trap proteins.

The term "fusion protein" refers to a molecule comprising two or more proteins or fragments thereof linked by a covalent bond via their individual peptide backbones, optionally generated through genetic expression of a polynucleotide molecule encoding the fusion protein.

In some embodiments, the protein of interest is a trap protein or a mini trap protein. In some embodiments, trap proteins are engineered therapeutic proteins capable of acting as decoy receptors to bind to and antagonize or modulate the activity of a target protein. An exemplary trap protein comprises one or more receptor components that mimic the binding domain of the receptor for its target protein (e.g., the VEGF receptor Ig domain 2 of Flt-1 and the Ig domain 3) fused to a human IgG constant region, optionally including additional domains such as linkers, dimerization or multimerization domains, and cleavage sites. In some embodiments, the trap protein is truncated or of reduced size (a mini trap), for example through protein cleavage, which can aid in tissue penetration of the mini trap. Non-limiting examples of trap proteins include an IL-1 trap (e.g., rilonacept, which contains the IL-1RAcP ligand binding region fused to the IL-1R1 extracellular region which in turn is fused to the Fc of hIgG1) (e.g., SEQ ID NO: 1) (see U.S. Pat. No. 6,927,004), or a VEGF trap (e.g., aflibercept, which contains the Ig domain 2 of the VEGF receptor Flt1 fused to the Ig domain 3 of the VEGF receptor Flk1 which in turn is fused to Fc of hIgG1. See, e.g., U.S. Pat. Nos. 7,087,411, 7,279,159; see also U.S. Pat. No. 5,610,279 for etanercept (TNF trap), the contents of each of which are incorporated by reference in their entirety herein.

Protein Production

The protein of interest assayed by the methods described herein can be produced by any method known in the art. For example, the protein of interest can be produced by cell cultures. The cell cultures can be a "fed-batch cell culture" or "fed-batch culture" which refers to a batch culture wherein the cells and culture medium are supplied to the culturing vessel initially and additional culture nutrients are slowly fed, in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture may be different from "perfusion culture" insofar as the supernatant is not removed from the culturing vessel during a standard fed-batch process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached, and protein is subsequently harvested.

The cell culture can be a "continuous cell culture" which is a technique used to grow cells continually, usually in a particular growth phase. For example, if a constant supply of cells is required, or the production of a particular protein of interest is required, the cell culture may require maintenance in a particular phase of growth. Thus, the conditions must be continually monitored and adjusted accordingly in order to maintain the cells in that particular phase.

The cells are cultured in cell culture medium. The terms "cell culture medium" and "culture medium" refer to a nutrient solution used for growing mammalian cells that typically provides the necessary nutrients to enhance growth of the cells, such as a carbohydrate energy source, essential (e.g., phenylalanine, valine, threonine, tryptophan, methionine, leucine, isoleucine, lysine, and histidine) and nonessential (e.g., alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g., serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e., have a known chemical structure). Chemically defined medium is entirely free of animal-derived components, such as serum- or animal-derived peptones. In one embodiment, the medium is a chemically defined medium.

A "cell line" refers to a cell or cells that are derived from a particular lineage through serial passaging or subculturing of cells. The term "cells" is used interchangeably with "cell population." The term "cell" includes any cell that is suitable for expressing a recombinant nucleic acid sequence. Cells include those of prokaryotes and eukaryotes, such as bacterial cells, mammalian cells, human cells, non-human animal cells, avian cells, insect cells, yeast cells, or cell fusions such as, for example, hybridomas or quadromas. In certain embodiments, the cell is a human, monkey, ape, hamster, rat or mouse cell. In other embodiments, the cell is selected from the following cells: Chinese Hamster Ovary (CHO) (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK21), HeLa, HepG2, WI38, MRC 5, Colo25, HB 8065, HL-60, lymphocyte, e.g., Jurkat (T lymphocyte) or Daudi (B lymphocyte), A431 (epidermal), U937, 3T3, L cell, C127 cell, SP2/0, NS-0, MMT cell, stem cell, tumor cell, and a cell line derived from an aforementioned cell. In some embodiments, the cell comprises one or more viral genes, e.g., a retinal cell that expresses a viral gene (e.g., a PER.C6® cell). In some embodiments, the cell is a CHO cell. In other embodiments, the cell is a CHO K1 cell.

Cells can be transformed with heterologous polynucleotides encoding a protein of interest using any method known in the art, including, but not limited to, transformation, transfection, electroporation, and the like.

The term "heterologous polynucleotide" refers a polynucleotide sequence encoding a heterologous nucleotide sequence not found in the wild type cell, which can include a sequence encoding the protein of interest. Exemplary heterologous polynucleotides include vectors comprising a sequence encoding the protein of interest, including, but not limited to, plasmid, phage and viral particles. Optionally, the vector allows transfer of a particular nucleic acid molecule to a cell. When introduced into an appropriate cell, an expression vector contains the necessary genetic elements to direct expression of the protein of interest. Exemplary vectors can include transcriptional promoter elements (i.e., an expression control sequence), which are operatively linked to the sequence encoding the protein of interest. The vector may be composed of either DNA, or RNA, or a combination of the two (e.g., a DNA-RNA chimera). Optionally, the vector may include a polyadenylation sequence, one or more restriction sites as well as one or more selectable markers such as phosphotransferase or hygromycin phosphotransferase. Additionally, depending on the cell type chosen and the vector employed, other genetic elements such as an origin of replication, additional nucleic acid restriction sites, enhancers, and sequences conferring inducibility of transcription, may also be incorporated into the vector. Selection of appropriate vectors and transformation methods will be apparent to those of ordinary skill in the art.

Glycosylation

In some embodiments, the protein of interest is glycosylated. The glycosylation can included N-linked glycosylation, O-linked glycosylation or a combination thereof. Many proteins and polypeptides of interest produced in cell culture are glycoproteins that contain covalently linked carbohydrate structures including oligosaccharide chains (glycans). These oligosaccharide chains are linked to the protein in the endoplasmic reticulum and the Golgi apparatus via either N-linkages or O-linkages. The oligosaccharide chains may comprise a significant portion of the mass of the glycoprotein. The oligosaccharide chains can play roles including facilitating correct folding of the glycoprotein, mediating protein-protein interactions, conferring stability, conferring advantageous pharmacodynamic and/or pharmacokinetic properties, inhibiting proteolytic digestion, targeting the glycoprotein to the proper secretory pathway and targeting the glycoprotein to a particular organ or organs.

In some embodiments, the protein of interest comprises N-linked glycosylation. Generally, N-linked oligosaccharide chains are added to the nascent, translocating protein in the lumen of the endoplasmic reticulum. The oligosaccharide is added to the amino group on the side chain of an asparagine residue contained within a target consensus sequence such as Asn-X-Ser/Thr or in some instances Asn-X-Cys, where X may be any amino acid except proline. The initial oligosaccharide chain is usually trimmed by specific glycosidase enzymes in the endoplasmic reticulum, resulting in a short, branched core oligosaccharide composed of two N-acetylglucosamine and three mannose residues.

After initial processing in the endoplasmic reticulum, the glycoprotein may undergo further processing before being secreted to the cell surface. N-linked oligosaccharide chains may be modified by the addition of mannose residues, resulting in a high-mannose oligosaccharide. Alternatively, one or more monosaccharides units of N-acetylglucosamine may be added to the core mannose subunits to form complex oligosaccharides. Galactose may be added to the N-acetylglucosamine subunits, and sialic acid subunits may be added to the galactose subunits, resulting in chains that terminate with either a sialic acid, a galactose or an N-acetylglucosamine residue. Additionally, a fucose residue may be added to an N-acetylglucosamine residue of the core oligosaccharide. Each of these additions is catalyzed by specific glycosyl transferases.

In addition to being modified by the N-linked glycosylation pathway, glycoproteins may also be modified by the addition of O-linked oligosaccharide chains to specific serine or threonine residues as they are processed in the Golgi apparatus. The residues of an O-linked oligosaccharide are added one at a time and the addition of each residue is catalyzed by a specific enzyme. In contrast to N-linked glycosylation, the consensus amino acid sequence for O-linked glycosylation is less well defined. In some embodiments, the protein of interest comprises O-linked glycosylation. In some embodiments, the O-linked glycosylation comprises the attachment of a sugar molecular to a serine (Ser) or Threonine (Thr) amino acid of the protein of interest.

In some embodiments, the protein of interest is a glycosylated protein. In some embodiments the glycosylated protein comprises at least one attached glycan. In some embodiments the protein of interest comprises at least 1 attached glycan, at least 2 attached glycans, at least 3 attached glycans, at least 4 attached glycans, at least 5 attached glycans, at least 6 attached glycans, at least 7 attached glycans, at least 8 attached glycans, at least 9 attached glycans, at least 10 attached glycans, at least 11 attached glycans, at least 12 attached glycans, at least 15 attached glycans, at least 20 attached glycans or at least 25 attached glycans. In some embodiments, the protein of interest has 1, 2, 3, 4, 5, 6, 7, 8, 9, 10, 11, 12, 13, 14, 15, 16, 17, 18, 19, 20, 21, 22, 23, 24 or 25 attached glycans. In some embodiments, the glycans are N-linked. In some embodiments, the glycans are O-linked. In some embodiments, the protein of interest comprises both N- and O-linked glycans.

In some embodiments, the protein of interest is a glycosylated protein. In some embodiments, the protein of interest comprises at least one glycosylation site. In some embodiments, the protein of interest comprises at least one glycosylation site, at least two glycosylation sites, at least 3 glycosylation sites, at least 4 glycosylation sites, at least 5 glycosylation sites, at least 6 glycosylation sites, at least 7 glycosylation sites, at least 8 glycosylation sites, at least 9 glycosylation sites, at least 10 glycosylation sites, at least 10 glycosylation sites, at least 11 glycosylation sites, at least 12 glycosylation sites, at least 15 glycosylation sites, at least 20 glycosylation sites or at least 25 glycosylation sites. In some embodiments, the at least glycosylation site is an N-linked glycosylation site, for example an asparagine within the N-linked glycosylation consensus sequence. In some embodiments, the at least one glycosylation site is an O-linked glycosylation site, for example a serine or threonine. In some embodiments, the protein of interest comprises both at least one N-linked glycosylation site and at least one O-linked glycosylation site.

In some embodiments, glycans comprise at least at least 0.5%, 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65% or at least 75% of the total weight of the glycosylated protein (5% weight/weight, or w/w). In some embodiments, glycans comprise at least 5% of the total weight of the glycosylated protein (5% w/w). In some embodiments, glycans comprise at least 10% of the total weight of the glycosylated protein (10% w/w). Methods of determining the percentage of protein weight made up of glycans will be readily apparent to one of ordinary skill in the art and include, but are not limited to, comparing expected weight derived from amino acid sequence to actual weight determined by the electrophoresis analysis methods described herein.

Reference Standards

In some embodiments, a reference standard is subjected to the same methods of preparation in parallel to the sample comprising the protein of interest, and analyzed in parallel to the sample comprising the protein of interest. In some embodiments, methods comprise comparing one or more characteristics of the protein of interest to the reference standard. For example, the methods can include comparing electropherograms of the protein of interest and the reference standard.

As used herein, a "reference standard" refers to a sample comprising a protein that has previously been analyzed using the methods known in the art, and whose characteristics are known. Known characteristics can be determined from the amino acid sequence of the reference standard (e.g., predicted molecular weight), or experimentally determined (e.g., electropherogram profile). These characteristics can include, but are not limited to, expected and experimentally determined molecular weight, electropherogram(s) generated using the methods described herein or known methods in the art, isoelectric point, extinction coefficient (a measure of how strongly the protein of interest absorbs light at a given wavelength), number of glycosylation sites, and molecular weight of attached glycans. A reference standard may be similar in one or more characteristics to a protein of interest. For example, both the protein of interest and the reference standard may be monoclonal antibodies, or comprise an Fc domain, be of similar molecular weight, or the like.

In some embodiments, the reference standard comprises the protein of interest. For example, the reference standard can be from a separate batch of the protein of interest than the sample, which has been previously characterized and stored under controlled conditions to prevent degradation.

In some embodiments, the disclosure provides methods of preparing a sample comprising a protein of interest and a reference standard for analysis using electrophoresis, comprising (a) denaturing the sample and the reference standard; (b) labeling the protein of interest and the reference standard with a fluorescent label to produce a labeled sample and labeled reference standard; (c) quenching the labeling reaction s of the protein of interest and the reference standard, (d) deglycosylating the labeled sample and labeled reference standard with an endoglycosidase; and (e) performing electrophoresis on the labeled sample and labeled reference standard; wherein the sample and the reference standard are labeled and quenched in steps (b) and (c) prior to deglycosylation in step (d).

In some embodiments, the electrophoresis is microchip capillary electrophoresis (MCE), and the output is an electropherogram. In some embodiments, the methods comprise determining a main peak intensity for the protein of interest and the reference standard, and comparing the intensity values of the main peak for the protein of interest and the main peak for the reference standard. In some embodiments, the main peak of the protein of interest or the reference standard is glycosylated. In some embodiments, the main peak of the protein of interest or the reference standard is not glycosylated, i.e., has been deglycosylated after labeling using the methods described herein. In some embodiments, determining the main peak comprises determining the height of the main peak. In some embodiments, determining the main peak comprises determining the area of the main peak. In some embodiments, determining the main peak comprises determining the time corrected area of the main peak, which is the peak area divided by its migration time. In some embodiments, the main peak intensity of the protein of interest is within 50% to 150%, 50% to 140%, 50% to 130%, 50% to 120%, 50% to 110%, 50% to 100%, 50% to 90%, 60% to 150%, 70% to 150%, 80% to 150%, 90% to 150%, 100% to 150%, 110% to 150%, 120% to 150%, 130% to 150%, 140% to 150%, 60% to 140%, 70% to 140%, 70% to 130%, 70% to 120%, 70% to 110%, 80% to 140%, 80% to 130%, 80% to 120%, 80% to 110%, 80% to 100%, 90% to 140%, 90% to 130%, 90% to 120%, 90% to 110% or 90% to 100% of the main peak intensity of the reference standard. In some embodiments, the main peak intensity of the protein of interest is within 60% to 140%, 70% to 130%, 80% to 120%, or 90% to 110% of the main peak intensity of the reference standard. In some embodiments, the main peak intensity of the protein of interest is within 70% to 130% of the main peak intensity of the reference standard. Determining main peak intensity of the protein of interest relative to the reference standard can ensure proper separation by the CE or MCE instrument, and data quality.

Electrophoresis

Provided herein are methods of analyzing a sample comprising a protein of interest prepared using the methods described herein using electrophoresis.

Electrophoresis based methods for analyzing proteins include, but are not limited to, gel-based methods such as sodium dodecyl (lauryl) sulfate (SDS) polyacrylamide gel electrophoresis (SDS-PAGE), polyacrylamide gel electrophoresis in the presence of lithium dodecyl sulfate, free-flow electrophoresis, isoelectric focusing, capillary gel electrophoresis, capillary electrophoresis (CE) and microchip capillary electrophoresis (MCE).

In some embodiments, the electrophoresis is CE. In some embodiments, the CE comprises a lithium dodecyl sulfate (LDS) buffer.

In some embodiments, the electrophoresis is MCE. The terms "MCE" or "Microchip Capillary Electrophoresis" and "capillary electrophoresis (CE)" refer to capillary electrophoresis (CE) and its microfluidic counterpart (MCE), which are used to separate analytes in a sample. MCE techniques can be used to separate, identify, and quantify proteins of interest, impurities in the protein sample, and analyze breakdown products of the protein of interest such as protein fragments. CE and MCE separate analytes based on electrophoretic mobility when a voltage is applied to a sample. The presence of gel matrix (e.g., gel electrophoresis) will separate analytes based on size as well as charge. Impurities in the sample include, but are not limited to protein aggregates, protein fragments, protein multimers, and assay contaminants.

In MCE, the denatured labeled protein of interest is diluted and subjected to MCE to separate the diluted protein sample on a microchip capillary electrophoresis system to produce an electropherogram. Because multiple samples can be run in parallel on the same microchip, MCE based methods are readily adaptable to high throughput approaches. Further, MCE is rapid, and uses minimal sample volume.

As used herein, an electropherogram is a plot that results from electrophoretic methods such as CE or MCE. The electropherogram contains peaks corresponding to the protein of interest and impurities.

Methods of analyzing electropherograms are known in the art, and include comparing the position, size and areas under individual peaks. Methods of calculating peak area for an electropherogram (area under the peak) are known in the art, and include, for example, integrating to estimate the area under a peak. Peak area can be calculated using software such as Empower.

Instrumentation for conducting the disclosed MCE assays is commercially available. In some embodiments, the disclosed MCE assays are performed using LabChip GXII, LabChip GXII Touch™, LabChip GXII Touch™ HT and a Protein Express Assay LabChip (LabChip® HT Protein Express Chip).

Instrumentation for conducting the disclosed CE assays is also commercially available. For example, CE assays can be performed using a Beckman Coulter capillary electrophoresis system such as the PA 800 Plus Pharmaceutical Analysis System.

In some embodiments of the methods described herein, the methods further comprise labeling and running a protein standard molecular weight ladder to assess the size of the protein of interest. Protein molecular weight ladders will be known to persons of ordinary skill in the art, and include PageRuler, Mark12, BenchMark, PageRuler High Range and PageRuler Low Range available from ThermoFisher, as well as the HT PICO Protein Express ladder from the Protein Pico Assay Reagent Kit from PerkinElmer. Selection of appropriate ladder based on size of the protein of interest will be apparent to one of ordinary skill in the art.

Applications

The disclosure provides methods of characterizing a protein of interest, using the methods of labeling, deglycosylation and electrophoresis described herein.

Analyzing a protein of interest can include, but is not limited to, characterizing the number, position, height, width, intensity, size or area of one or more peaks in an electropherogram generated by CE or MCE.

Characterizing the number and position of peaks in an electropherogram can determine whether or not degradation products of the protein of interest are present in the sample, for example as peaks with molecular weights that are less than that of the main peak. Comparison of peaks generated from non-deglycosylated protein of interest, and protein of interest deglycosylated and labeled using the methods described herein, can determine whether or not glycosylated forms of the protein of interest are present in the sample, as a deglycosylated main peak of the protein of interest will have a lower molecular weight than a glycosylated main peak of a protein of interest.

The methods of the instant disclosure can be used to assay the stability of proteins of interest under various conditions. These include storage conditions for protein of interest that has been formulated as a drug substance or drug product. Comparisons of peak number and peak area, for example between a reference sample comprising a protein of interest and a stressed sample thereof, can be used to determine the stability of the protein of interest over time, and under various conditions such as high or low pH, or exposure to light.

Accordingly, the disclosure provides methods of determining stability of a protein of interest using the methods of labeling and deglycosylating a protein of interest described herein. In some embodiments, the methods comprise (a) stressing a sample comprising the protein of interest; (b) denaturing the stressed sample and a non-stressed sample comprising the protein of interest; (c) labeling the protein of interest in the stressed sample and the non-stressed sample with a fluorescent label to produce a labeled stressed sample and a labeled non-stressed sample; (d) quenching un-reacted fluorescent label in the labeled stressed sample and the labeled non-stressed sample; (e) deglycosylating the labeled stressed sample and the labeled non-stressed sample with an endoglycosidase; (f) performing microchip capillary electrophoresis (MCE) on the labeled stressed sample and the labeled non-stressed sample to generate electropherograms for the stressed sample and the non-stressed sample; and (g) comparing the electropherograms from the stressed sample and the nonstressed sample; wherein the stressed sample and the non-stressed sample are labeled and quenched in steps (c) and (d) prior to deglycosylation in step (e).

Any methods of stressing a protein of interest in a sample are envisaged as within the methods of the disclosure, including, but not limited to, chemicals, pH, radiation, light, freeze-thaw cycles, lyophilization and heat.

In some embodiments, stressing the sample comprising the protein of interest comprises thermally stressing the sample. Thermally stressing the sample can include simulating storage conditions for protein of interest formulated as drug substance or formulated drug product, i.e. the stressed sample is held at about −80° C. to −30° C. or about 2° C. to about 8° C., respectively. In other embodiments, thermally stressing the sample comprises simulating handling and transport conditions for the sample. In other embodiments, thermally stressing the sample comprises inducing forced degradation of the sample, for example by increasing the temperature to which the sample is exposed.

In some embodiments, stressing the sample comprising the protein of interest comprises thermally stressing the sample. In some embodiments, the thermal stress comprises holding the sample between 25° C. and 45° C. In some embodiments, the thermal stress comprises holding the sample at 2° C., 4° C., 6° C., 8° C., 10° C., 12° C., 14° C., 16° C., 18° C., 20° C., 22° C., 24° C., 26° C., 28° C., 30° C., 32° C., 35° C., 37° C. or 40° C. In some embodiments, the thermal stress comprises holding the sample at 37° C. In some embodiments, the thermal stress comprises holding the sample at 22° C. to 26° C. In some embodiments, the thermal stress comprises holding the sample at 30° C. In some embodiments, the thermal stress comprising holding the protein at between about 25° C. and 45° C. In some embodiments, the thermal stress comprises holding the stressed sample for at least 1 week, 2 weeks, 3 weeks 4 weeks, 5 weeks, 6 weeks, 7 weeks, 8 weeks 9 weeks, 10 weeks, 3 months, 4 months, 5 months, 6 months, 7 months, 8 months, 9 months, 10 months, 11 months or one year. In some embodiments, the stressed sample is held for 2 weeks. In some embodiments, the stressed sample is held for 4 weeks.

In some embodiments, thermally stressing the sample comprises holding the sample at between about 25° C. and about 45° C. for at least 1 week, at least 2 weeks, at least 3 weeks, at least 4 weeks, at least 5 weeks, at least 6 weeks, at least 7 weeks or at least 8 weeks. In some embodiments, thermally stressing the sample comprises holding the sample at between about 30° C. and about 45° C. for at least 1 week, at least 2 weeks, at least 3 weeks, at least 4 weeks, at least 5 weeks, at least 6 weeks, at least 7 weeks or at least 8 weeks.

In some embodiments, stressing the sample comprises at least one freeze/thaw cycle. For example, starting from a liquid sample, lowering the temperature until the sample freezes, and then returning the sample to a temperature where it is a liquid prior to analysis.

In some embodiments, stressing the sample comprises exposing the sample to storage conditions. In some embodiments, the storage conditions comprise a temperature of about −80° C. to −30° C. for at least 1 week, at least 2 weeks, at least 3 weeks, at least 1 month, at least 2 months, at least 3 months, at least 6 months, at least 8 months, at least 12 months, at least 18 months, at least 24 months or at least 30 months. In some embodiments, the storage conditions comprise a temperature of about 2° C. to 8° C. for at least 1 week, at least 2 weeks, at least 3 weeks, at least 1 month, at least 2 months, at least 3 months, at least 6 months, at least 8 months, at least 12 months or at least 18 months.

In some embodiments, stressing the sample comprises mechanically agitating the sample, for example using a Vortex or magnetic stirrer.

In some embodiments, stressing the sample comprises lyophilizing and rehydrating the sample. Methods of lyophilizing a sample comprising a protein of interest will be known to persons of ordinary skill in the art and include, for example freeze drying and spray drying.

In some embodiments, stressing the sample comprises exposing the sample to light, radiation, singlet oxygen species, free radicals, high pH conditions or low pH conditions. Exemplary low pH conditions include, inter alia, exposing the sample to a pH of less than 7.0, for example a pH of less than 6.0, 5.5, 5.0, 4.5, 4.0, 3.5, 3.0, 2.0, 1.5 or 1.0. Exemplary high pH conditions include, inter alia, exposing the sample to a pH of greater than 7.0, for example a pH of greater than 8.0, 8.5, 9.0, 9.5 or 10.0.

In some embodiments, stressing the sample comprises exposing the sample to light. Exposure to light can include light of any wavelength, or any range of wavelengths. In exemplary embodiments, samples are expose to cool white fluorescent light or near ultraviolet light. Exemplary cool white fluorescent light comprises light of mixed wavelengths that has a correlated color temperature (CCT) of about 4,100 to about 4,500 kelvins (K). In some aspects, the cool white fluorescent light has a CCT of 4,100K. In some aspects, exposing the sample to light comprises exposing the sample to about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 million lux hours accumulated exposure of cool white light. In some aspects, exposing the sample to light comprises exposing the sample to about 1.2 or about 2.4 million lux hours accumulated exposure of cool white light. Exemplary near ultraviolet light has a wavelength of about 300 nm to about 400 nm. In some aspects, the near ultraviolet light has an integrated energy of between about 100 watt hours/square meter to about 600 watt hours/square meter. In some aspects, the near ultraviolet light has an integrated energy of about 100, 200, 300, 400, 500 or 600 watt hours/square meter.

A reduction in main peak area between the reference sample and the stressed version thereof can, for example, indicate a reduction of protein of interest in the main peak through degradation. In some embodiments, the area of the main peak of the stressed protein of interest is reduced by at least 1%, at least 2%, at least 3%, at least 4%, at least 5%, at least 6 at least 7%, at least 8%, at least 9%, at least 10%, at least 15%, at least 20%, at least 25%, at least 30%, at least 35% or at least 40% compared to the main peak of the non-stressed protein of interest. Similarly, an increase in the area of low molecular weight peaks in the stressed reference sample compared to the reference sample can indicate degradation of the protein of interest, as the abundance of the lower molecular weight species representing degradation products of the protein of interest increases. In some embodiments, the area of at least one low molecular weight peak of the stressed protein of interest is increased by at least 1%, at least 2%, at least 3%, at least 4%, at least 5%, at least 6 at least 7%, at least 8%, at least 9%, at least 10%, at least 15%, at least 20%, at least 25%, at least 30%, at least 35% or at least 40% compared to at least one low molecular weight peak of the non-stressed protein of interest.

Kits and Articles of Manufacture

The disclosure provides kits including one or more the disclosed buffers, enzymes, dyes and reference standards used in the methods of deglycosylation and labeling described herein. The kits can include a container for the ingredients. The buffers can be in solution or in lyophilized form. In some embodiments, the kits include a second container containing a diluent or reconstituting solution for the lyophilized formulation; and optionally, instructions for the use of the solution or the reconstitution and/or use of the lyophilized buffers or powdered ingredients.

The kits described herein may further include additional reagents needed to perform the disclosed MCE assays including one or more of a buffer, a diluent, and a filter. The buffer and reagents can be in a bottle, a vial, or test tube.

In some embodiments, the kits include instructions for use.

The present description sets forth numerous exemplary configurations, methods, parameters, and the like. It should be recognized, however, that such description is not intended as a limitation on the scope of the present disclosure, but is instead provided as a description of exemplary embodiments.

ENUMERATED EMBODIMENTS

The invention may be defined by reference to the following enumerated, illustrative embodiments:

1. A method of analyzing a sample comprising a protein of interest, the method comprising:
  a. denaturing the sample;
  b. labeling the sample with a fluorescent label to produce a labeled sample;
  c. quenching un-reacted fluorescent label in the labeled sample;
  d. deglycosylating the labeled sample with an endoglycosidase; and
  e. performing electrophoresis on the labeled sample;
  wherein the sample is denatured, labeled and quenched in steps (a) through (c) prior to deglycoslation in step (d).
2. The method of embodiment 1, wherein the protein of interest comprises at least one glycosylation site.
3. The method of embodiment 1 or 2, wherein the protein is of interest is a glycosylated protein.
4. The method of embodiment 3, wherein the glycosylated protein comprises at least one attached glycan.
5. The method of any one of embodiments 1-4, wherein the protein of interest comprises an antigen binding domain.
6. The method of embodiment 5, wherein the protein of interest comprises an antibody, an antibody fragment or an scFv.
7. The method of any one of embodiments 1-6, wherein the protein of interest comprises an Fc domain.
8. The method of any one of embodiments 1-7, wherein the protein of interest comprises a receptor fusion protein.
9. The method of embodiment 8, wherein the receptor fusion protein is a receptor-Fc-fusion protein or a soluble TCR-Fc fusion protein.
10. The method of embodiment 8 or 9, wherein the receptor fusion protein is a trap protein or a mini trap protein.
11. The method of any one of embodiments 1-10, wherein the protein of interest is a recombinant human protein.
12. The method of any one of embodiments 2-11, wherein the glycosylation site comprises an Asn-X-Ser/Thr consensus sequence.
13. The method of any one of embodiments 4-12, wherein the at least one attached glycan is N-linked.
14. The method of embodiment 13, wherein the at least one attached glycan is N-linked to an asparagine in the glycosylated protein.
15. The method of any one of embodiments 1-14, wherein the endoglycosidase catalyzes deglycosylation of N-linked glycans.
16. The method of embodiment any one of embodiments 1-15, wherein the endoglycosidase is selected from the group consisting of Peptide-N-Glycosidase F (PNGase F), Endoglycosidase H (Endo H), Endoglycosidase S (Endo S), Endoglycosidase D, Endoglycosidase F1, Endoglycosidase F2 and Endoglycosidase F4.
17. The method of any one of embodiments 1-15, wherein the endoglycosidase is PNGase F.
18. The method of embodiment 17, wherein the PNGase F is Rapid PNGase F.
19. The method of embodiment 18, wherein the Rapid PNGase F is non-reducing.
20. The method of any one of embodiments 17-19, wherein deglycosylating the sample comprises heating the sample to about 50° C. for 10 minutes.
21. The method of any one of embodiments 1-20, wherein deglycosylating the sample comprises a reaction mixture comprising between 0.2-1.5 mg labeled protein of interest, and between 1-5 µL Rapid PNGase F in a 10 µL reaction volume, excluding the volume of the Rapid PNGase F.
22. The method of embodiment 21, wherein the reaction mixture comprises 0.2 mg labeled protein of interest.
23. The method of embodiment 21, wherein the reaction mixture comprises 5 µL Rapid PNGase F.
24. The method of any one of embodiments 21-23, wherein the reaction mixture comprises a buffer.
25. The method of any one of embodiments 4-11, wherein the at least one glycan is an O-linked glycan.
26. The method of embodiment 25, wherein the endoglycosidase catalyzes deglycosylation of O-linked glycans.
27. The method of embodiment 25 or 26, wherein the endoglycosidase comprises Endo-α-N-acetylgalactosamindase (O-glycosidase).
28. The method of any one of embodiments 1-27, wherein labeling the sample with the fluorescent label comprises heating the sample to about 35° C. for 10-30 minutes.

29. The method of any one of embodiments 1-27, wherein labeling the sample with the fluorescent label comprises heating the sample to about 35° C. for about 15 minutes.
30. The method of any one of embodiments 1-29, wherein the sample is denatured using a reducing solution.
31. The method of embodiment 30, wherein the reducing solution comprises dithiothreitol (DTT).
32. The method of any one of embodiments 1-29, wherein the sample is denatured using a non-reducing solution.
33. The method of embodiment 32, wherein the non-reducing solution comprises iodoacetamide (IAM).
34. The methods of any one of embodiments 1-33, wherein denaturing the sample comprises heating the sample to between 40° C. and 99° C. for between 1 minute and 5 hours.
35. The methods of any one of embodiments 1-33, wherein denaturing the sample comprises heating the sample to between 50° C. and 99° C. for between 1 to 60 minutes.
36. The method of any one of embodiments 1-35, wherein quenching the un-reacted fluorescent label comprises adding a stop solution.
37. The method of any one of embodiments 1-36, further comprising analyzing a reference standard in parallel to the sample.
38. The method of any one of embodiments 1-37, wherein the electrophoresis is selected from the group consisting of gel electrophoresis, isoelectric focusing, capillary electrophoresis (CE) or microchip capillary electrophoresis (MCE).
39. The method of any one of embodiments 1-37, wherein the electrophoresis is MCE.
40. The method of embodiment 39, wherein the MCE is carried out using an MCE instrument.
41. The method of any one of embodiments 1-40, wherein method results in reduced free dye interference in the less than 20 kDa range and a reduced or absent endoglycosidase peak in an electropherogram when compared to an electropherogram generated using a sample labeled after deglycosylation.
42. The method of embodiment 41, wherein the endoglycosidase peak is reduced by at least 5%, at least 10%, at least 20%, at least 30%, at least 40%, at least 50%, at least 60%, at least 70%, at least 80% or at least 90% when compared to an electropherogram generated using a sample labeled after deglycosylation.
43. The method of embodiment 41, wherein the endoglycosidase peak is absent in an electropherogram when compared to an electropherogram generated using a sample labeled after deglycosylation.
44. A method of determining stability of a protein of interest comprising:
a. stressing a sample comprising the protein of interest;
b. denaturing the stressed sample and a non-stressed sample comprising the protein of interest;
c. labeling the stressed sample and the non-stressed sample with a fluorescent label to produce a labeled stressed sample and a labeled non-stressed sample;
d. quenching un-reacted fluorescent label in the labeled stressed sample and the labeled non-stressed sample;
e. deglycosylating the labeled stressed sample and the labeled non-stressed sample with an endoglycosidase;
f. performing microchip capillary electrophoresis (MCE) on the labeled stressed sample and the labeled non-stressed sample to generate electropherograms for the stressed sample and the non-stressed sample; and
g. comparing the electropherograms from the stressed sample and the nonstressed sample, thereby determining the stability of the protein of interest;
wherein the stressed sample and the non-stressed sample are denatured, labeled and quenched in steps (b) through (d) prior to deglycoslation in step (e).
45. The method of embodiment 44, wherein stressing the sample comprises thermally stressing the sample.
46. The method of embodiment 45, wherein thermally stressing the sample comprises holding the sample at between about 30° C. and about 45° C. for at least 1 week, at least 2 weeks, at least 3 weeks, at least 4 weeks, at least 5 weeks, at least 6 weeks, at least 7 weeks or at least 8 weeks.
47. The method of embodiment 44, wherein stressing the sample comprises at least one freeze/thaw cycle.
48. The method of embodiment 44, wherein stressing the sample comprises exposing the sample to storage conditions.
49. The methods of embodiment 48, wherein the storage conditions comprise a temperature of about −80° C. to −30° C. for at least 1 week, at least 2 weeks, at least 3 weeks, at least 1 month, at least 2 months, at least 3 months, at least 6 months, at least 8 months, at least 12 months, at least 18 months, at least 24 months or at least 30 months.
50. The methods of embodiment 48, wherein the storage conditions comprise a temperature of about 2° C. to 8° C. for at least 1 week, at least 2 weeks, at least 3 weeks, at least 1 month, at least 2 months, at least 3 months, at least 6 months, at least 8 months, at least 12 months or at least 18 months.
51. The method of embodiment 44, wherein stressing the sample comprises mechanically agitating the sample.
52. The method of embodiment 44, wherein stressing the sample comprises lyophilizing and rehydrating the sample.
53. The method of embodiment 44, wherein stressing the sample comprises exposing the sample to light, radiation, singlet oxygen species, free radicals, high pH conditions or low pH conditions.
54. The method of any one of embodiments 44-53, wherein the protein of interest comprises at least one glycosylation site.
55. The method of any one of embodiments 44-53, wherein the protein is of interest is a glycosylated protein.
56. The method of embodiment 55, wherein the glycosylated protein comprises at least one attached glycan.
57. The method of any one of embodiments 44-56, wherein the protein of interest comprises an antigen binding domain.
58. The method of embodiment 57, wherein the protein of interest comprises an antibody, an antibody fragment or an scFv.
59. The method of any one of embodiments 44-58, wherein the protein of interest comprises an Fc domain.
60. The method of any one of embodiments 44-59, wherein the protein of interest comprises a receptor fusion protein.
61. The method of embodiment 60, wherein the receptor fusion protein is a receptor-Fc-fusion protein or a soluble TCR-Fc fusion protein.
62. The method of embodiment 60 or 61, wherein the receptor fusion protein is a trap protein or a mini trap protein.

63. The method of any one of embodiments 44-62, wherein the protein of interest is a recombinant human protein.
64. The method of any one of embodiments 54-63, wherein the glycosylation site comprises an Asn-X-Ser/Thr consensus sequence.
65. The method of any one of embodiments 56-64, wherein the at least one attached glycan is N-linked.
66. The method of embodiment 65, wherein the at least one attached glycan is N-linked to an asparagine in the glycosylated protein.
67. The method of any one of embodiments 44-66, wherein the endoglycosidase catalyzes deglycosylation of N-linked glycans.
68. The method of embodiment any one of embodiments 44-67, wherein the endoglycosidase is selected from the group consisting of Peptide-N-Glycosidase F (PNGase F), Endoglycosidase H (Endo H), Endoglycosidase S (Endo S), Endoglycosidase D, Endoglycosidase F1, Endoglycosidase F2 and Endoglycosidase F4.
69. The method of any one of embodiments 44-67, wherein the endoglycosidase is PNGase F.
70. The method of embodiment 69, wherein the PNGase F is Rapid PNGase F.
71. The method of embodiment 70, wherein the Rapid PNGase F is non-reducing.
72. The method of any one of embodiments 44-71, wherein deglycosylating the stressed and non-stressed samples comprises heating the samples to about 50° C. for 10 minutes.
73. The method of any one of embodiments 44-72, wherein deglycosylating the stressed and non-stressed samples comprises a reaction mixture for each sample comprising between 0.2-1.5 mg labeled protein of interest, and between 1-5 μL Rapid PNGase F in a 10 μL reaction volume excluding the volume of the Rapid PNGase F.
74. The method of embodiment 73, wherein the reaction mixture for each of the stressed and non-stressed sample comprises 5 μL Rapid PNGase F.
75. The method of embodiment 73 or 74, wherein each of the stressed and non-stressed sample comprise 0.2 mg labeled protein of interest.
76. The method of any one of embodiments 73-75, wherein the reaction mixture for each of the stressed and non-stressed sample comprises a buffer.
77. The method of any one of embodiments 44-63, wherein the at least one glycan is an O-linked glycan.
78. The method of embodiment 77, wherein the endoglycosidase catalyzes deglycosylation of O-linked glycans.
79. The method of embodiment 77 or 78, wherein the endoglycosidase comprises Endo-α-N-acetylgalactosamindase (O-glycosidase).
80. The method of any one of embodiments 44-79, wherein labeling the stressed and non-stressed samples with the fluorescent label comprises heating each sample to about 35° C. for 10-30 minutes.
81. The method of any one of embodiments 44-79, wherein labeling the stressed and non-stressed samples with the fluorescent label comprises heating each sample to about 35° C. for about 15 minutes.
82. The method of any one of embodiments 44-81, wherein the stressed and non-stressed samples are denatured using a reducing solution.
83. The method of embodiment 82, wherein the reducing solution comprises dithiothreitol (DTT).
84. The method of any one of embodiments 44-81, wherein the stressed and non-stressed samples are denatured using a non-reducing solution.
85. The method of embodiment 84, wherein the non-reducing solution comprises iodoacetamide (IAM).
86. The method of any one of embodiments 44-85, wherein denaturing the stressed and non-stressed samples comprises heating the samples to between 40° C. and 99° C. for between 1 minute and 5 hours.
87. The method of any one of embodiments 44-85, wherein denaturing the stressed and non-stressed samples comprises heating the samples to between 50° C. and 99° C. for between 1 to 60 minutes.
88. The method of any one of embodiments 44-87, wherein quenching the un-reacted fluorescent label comprises adding a stop solution.
89. The method of any one of embodiments 44-88, further comprising analyzing a reference standard in parallel to the stressed and non-stressed samples.
90. The method of any one of embodiments 44-89, wherein comparing the electropherograms for the stressed and non-stressed samples comprises comparing peak number, height, position, area, or a combination thereof.

EXAMPLES

Example 1: Reagents

Materials and Equipment

TABLE 1

| Materials (equivalent items can also be used) | |
|---|---|
| Item | Vendor Information and Handling |
| Safe-Lock Eppendorf tubes, 1.5 mL | VWR, cat. # 21008-959 or 20901 548 |
| 96 well low skirted plates | BioRad PN HSP-9621 |
| Millipore Ultrafree MC GV Durapore PVDF 0.22 μM, or National Microcentrifugal Filters, Non-sterile | Cat. UFC30GVNB or Thermo Scientific (VWR Cat. 66064-450) |
| TX761 Swabs | VWR PN TWTX761 |
| VWR ® Heat-Resistant Polypropylene Film for Raised-Rim Plates | PN 89087-69 |
| Lint Free Cloth | Wypall L40 PN Os701/7471 |
| VWR Reagent Reservoir | VWR 89094-674 |
| Nalgene ® Bottle Top Filters, PES Membrane, Sterile | Thermo Scientific (VWR73521-002) |
| Protein Express LabChip, LabChip ® GXII, | PN 760499 or 760528; |

TABLE 1-continued

Materials (equivalent items can also be used)

| Item | Vendor Information and Handling |
| --- | --- |
| LabChip ® GXII Touch ™ HT | Store between 2-8° C. until use. Allow chip to warm for 30 min at room temperature before first time use. Once at room temperature, assign a 30 day expiration date to the chip. |

TABLE 2

Chemicals (equivalent items can also be used)

| Chemical | Vendor Information and Handling |
| --- | --- |
| Water, purified by MilliQ | — |
| Protein Reference Standard | Reference Standards be specific to an assay or experimental program, or universal |
| 0.2M Sodium Phosphate pH 8.0 | VWR Cat. No. J62733 |
| 10X Reducing Agent (0.5M dithiothreitol) | Novex Life Technologies PN NP0009; When received dispense stock as 1 mL aliquots and store between 2 and 8° C. Each vial should be used once and assigned a 6 month expiration |
| Iodoacetamide (IAM) | Sigma, A3221-10VL; Sigma, I1149 (MW 184.96) (Store as a solid between 2 and 8° C.) |
| Pico Protein Reagent Kit | Perkin Elmer PN 760498; The kit contains the following (vial cap colors indicated and used throughout): Pico 5X Labeling Buffer (1 vial) (clear) Lyophilized Labeling Dye (4 vials) (blue) Sample Buffer (5 vials) (white) Protein Gel Matrix (2 vials) (red) Protein Ladder (1 vial) (yellow) Lower Marker (1 vial) (green) Wash Buffer (4 vials) (purple) Stop Buffer (1 vial) (orange) DMSO (Dimethyl sulfoxide) (1 vial) (brown) All reagents are stored between 2° C. and 8° C. except the Lyophilized Labeling Dye, which is stored at ≤−20° C. until reconstituted. The kit must be held at room temperature for a minimum of 30 min prior to use. |
| Sodium Phosphate Monobasic Monohydrate | Sigma Aldrich Cat. No. 71504; (MW 137.99) Store at room temperature |
| Sodium Phosphate Dibasic Heptahydrate | Sigma Aldrich Cat. No. S2429; (MW 268.07) Store at room temperature |
| Lithium Dodecyl Sulfate (LDS) | Sigma Aldrich Cat. No. L9781; (FW 272.33) (Store at room temperature) |
| 70% Isopropanol (VWR 89108-160) or Isopropanol | for cleaning (Store at room temperature) |

TABLE 3

Equipment

| Item | Vendor Information and Handling |
| --- | --- |
| Appropriate volume pipettes and vendor tips or equivalent | VWR, Rainin or Gilson |
| Microcentrifuge Eppendorf Model 5424 or equivalent | — |
| Plate Centrifuge Model 5804 equipped for 96 well plates or equivalent | — |
| Eppendorf Thermomixer for Eppendorf tubes or Eppendorf Nexus Master Cycler with Flex lid for 96 well plates or equivalent | — |
| Lab Chip GXII Perkin Elmer or Lab Chip GXII Touch HT | — |
| Vortex or equivalent | — |

TABLE 3-continued

| | Equipment |
|---|---|
| Item | Vendor Information and Handling |
| Vacuum Aspiration Set up or equivalent | Example set up - 1000 μL pipet tip attached to a first piece of plastic tubing, the tubing attached to a stoppered Erlenmeyer flask as a liquid reservoir, a second tube attaching the flask to a vacuum source. The pipet tip is replaced after each cleaning step (e.g., aspiration pass, sipper test) |

TABLE 4

| Reagent Solutions | |
|---|---|
| Reagent Solution | Preparation |
| Non-Reducing Solution:<br>272 μL 1M IAM<br>1328 μL 100 mM Sodium Phosphate 1% LDS, pH 6<br>40 μL MilliQ water | Prepare as a bulk solution and vortex to mix |
| 1M IAM (Iodoacetamide) | Add 303 μL MilliQ water to a 56 mg vial of IAM. Vortex until completely dissolved. Prepare fresh. |
| Reducing Solution:<br>476 μL 10 x Reducing Agent<br>1162 μL 100 mM Sodium Phosphate 1% LDS pH 9<br>42 μL MilliQ water | Prepare as a bulk solution and vortex to mix |
| Diluted Stop Solution:<br>2.5 μL Stop Buffer (orange cap)<br>17.1 μL Sample Buffer (white cap)<br>85.4 μL MilliQ water | Stop and Sample buffers from the Pico Protein Reagent Kit |
| 5 μM Dye:<br>10 μL of 100 μM Dye (frozen aliquots stored at −20° C.)<br>190 μL MilliQ water | Vortex 5 μM Dye Solution on high setting to dissolve. |
| 100 μM Dye | Spin Lyophilized Labeling Dye (blue cap, Pico Protein Reagent Kit) at 15,000 rpm for 1 min.<br>Add 240 μL of DMSO<br>Vortex on high setting until completely dissolved. |
| 200 mM Sodium Phosphate Monobasic Monohydrate | Add 5.5 g of Sodium Phosphate Monobasic Monohydrate to 200 mL of MilliQ water.<br>Mix until dissolved and filter through a 0.22 μm bottle top filter. |
| 200 mM Sodium Phosphate Dibasic Heptahydrate | Add 10.7 g of Sodium Phosphate Dibasic Heptahydrate to 200 mL of MilliQ water.<br>Mix until dissolved and filter through a 0.22 μm bottle top filter. |
| 10% LDS (lithium dodecyl sulfate) | Dissolve 1 g of LDS in 8 mL of MilliQ and QS with MilliQ to a total volume of 10 mL.<br>Filter through a 0.22 μm bottle top filter. |
| 100 mM Sodium Phosphate 1% LDS pH 6:<br>8.18 mL 200 mM Sodium Phosphate Monobasic Monohydrate<br>1.82 mL 200 mM Sodium Phosphate Dibasic Heptahydrate<br>2 mL 10% LDS<br>8 mL MilliQ water | Mix solution using a vortex. |
| 100 mM Sodium Phosphate 1% LDS pH 9:<br>10 mL 200 mM Sodium Phosphate Dibasic Heptahydrate<br>2 mL 10% LDS<br>8 mL MilliQ water | Mix solution using a vortex. |

TABLE 5

Summary of MCE methods

| MCE Method | Protocol | Description | Results |
|---|---|---|---|
| Method A | Example 2 | No deglycosylation, conventional sample preparation. | No peak resolution for heavily glycosylated protein; not stability indicating; Free dye interference at <20 kDa. |
| Method B | Example 3 | Deglycosylation prior to dye labeling | Good peak resolution; 3 hours deglycosylation, PNGase F peak interference, free dye interference at <20k Da. |
| Method C | Example 4 | Deglycosylation after dye labeling | Good peak resolution; no PNGase F peak in profile; 10 min deglycosylation, Resolution at 10-20 kDa, Stability indicating. |

TABLE 6

Summary of Proteins used in the Examples

| Protein | Used in Examples | Used in FIGs | MW (backbone peptide) | Number of N-glycosylation | Description |
|---|---|---|---|---|---|
| Protein 1 | 5, 6, 10 | 2-8, 14-15 | 49.4 | 8 | Disulfide linked recombinant (Fab')2-like trap protein |
| Protein 2 | 7 | 9 | 48 | 8 | Single Chain Recombinant (Fab')2-like trap protein |
| Protein 3 | 8 | 10-11 | 23 | 1 | Isolated Fc fragment |
| Protein 4 | 9 | 12-13 | 145 | 2 | IgG4 mAb |

Example 2: Protocol for Microchip Capillary Electrophoresis without Deglycosylation (Method A)

This protocol describes the preparation method for analysis of test proteins by non-reduced (NR) and reduced (R) Microchip Capillary Electrophoresis (MCE) using the GXII instrument to estimate purity and impurity levels. These methods are used for protein characterization or determining the level of fragmentation in a protein sample. These conventional methods are carried out without deglycosylation.

Procedure

See FIG. 1 for an information only flow path for this procedure.

(1) Denaturing. Dilute the protein reference standard or test article with water to about 0.2-2.0 mg/mL. In a 96-well plate, add the protein sample and Non-Reducing (NR)/Reducing (R) Solution at a volume ratio of 4:1 (volume can be varied). Seal the plate with polypropylene seal and heat the plate at a protein-specific denaturing temperature (typically 50 to 99° C.) for an optimized time (typically 1 to 60 minutes).

(2) Labeling. Prepare the 5 μM dye as described in Table 4. Add the 5 μM dye to the denatured protein solution at a volume ratio of 1:1 (volume can be varied). Heat the 96 well plate in a thermocycler at 35° C. for 30 minutes. To quench the labeling reaction, add 105 μL of diluted stop solution (prepared according to Table 4) and 5 μL of labeled protein to a new 96 well plate and mix well.

(3) Run on GX-II. Prepare the MCE instrument and microchip, and perform the measurements according to manufacturer's instructions.

Example 3: Protocol for Microchip Capillary Electrophoresis with Deglycosylation Before Protein Labeling (Method B)

This method applies to glycoproteins that need to be deglycosylated before subjected to MCE measurements. Unless otherwise specified, all protocols, chemicals, reagents and analysis are the same as described in Examples 1-2.

TABLE 7

Additional Reagents

| Reagent | Vendor Information |
|---|---|
| PNGase F | New England BioLabs NEB #P0704L |
| GlycoBuffer 2 (10X) Buffer | New England BioLabs, #B3704 |
| RapiGest SF Surfactant | Waters, PN 186001861 |
| Ammonium bicarbonate (ABC) | Sigma (Fluka), Cat#: 40867 |

Procedure (1) Deglycosylation. Dilute a total 100 μg of the protein sample with 0.1% RapiGest SF to 90 μL. Protein weight can be determined by UV based methods. Add 10 μL NEB PNGase F stock and make a 100 μL deglycosylation mixture, vortex and spin down. Incubate the mixture at 37° C. for 3 hours on a heating block with shaking at 400 revolutions per minute (rpm).

(2) Denaturing. Proceed with denaturing of the above-mentioned deglycosylated sample as described in Example 2.

(3) Labeling. Proceed with labeling the denatured sample as described in Example 2.

(4) Run on GX-II. Prepare the MCE instrument and microchip, and perform the measurements according to manufacturer's instructions.

Example 4: Protocol for Microchip Capillary Electrophoresis with Deglycosylation after Protein Labeling (Method C)

This method applies to glycoproteins that need to be deglycosylated before subjected to MCE measurements. Unless otherwise specified, all protocols, chemicals, reagents and analysis are the same as described in Examples 1-3.

A diagram of the protocol for deglycosylation after protein labeling can be seen in FIG. 1.

TABLE 8

| Additional Reagents | |
|---|---|
| Reagent | Vendor Information |
| Rapid ™ PNGase F (non-reducing format) | New England BioLabs NEB #P0710 |
| 5× Rapid ™ PNGase F Buffer (non-reducing format) | New England BioLabs NEB #B0717S |

Procedure (1) Denaturing. Dilute and denature the sample as described in Example 2.

(2) Labeling. Prepare the 5 μM dye as described in Table 4. Mix 5 μM dye and above-mentioned denatured protein solution at a volume ratio of 1:1. For example, if the volume of the sample is 10 add 10 μL of 5 μM dye. Seal the 96 well plate with a polypropylene seal and heat in the thermocycler at 35° C. for 30 minutes. For quenching the labeling reaction, obtain an unused 96-well plate. Add 2.5 μL stop buffer (orange cap vial from the Pico Protein Reagent Kit, use the original solution from the kit) to the wells of the empty plate according to the sample run set up. Transfer 2.5 μL of labeled sample to the plate wells containing the stop solution. Pipet mix sample in each well and hold for at least 3 minutes.

(3) Deglycosylation. Add to each well 3 μL MilliQ water and 2 μL 5× Rapid™ PNGase Buffer (non-reducing format from NEB) to make a 10 μL reaction volume. Add to each well 1-4 μL Rapid™ PNGase (non-reducing format from NEB). Seal the 96 well plate with a polypropylene seal and heat in the thermocycler at 50° C. for 10-30 minutes. After deglycosylation, add to each well 17 μL Sample Buffer (white cap vial from the Pico Protein Reagent Kit) and 80 μL MilliQ water.

(4) Run on GX-II. Prepare the MCE instrument and microchip, and perform the measurements according to manufacturer's instructions.

Example 5: Comparing No Deglycosylation and Deglycosylation Before Protein Labeling Using a Heavily Glycosylated, Sialic Acid Containing Protein Protein 1 is a disulfide linked recombinant fusion protein which is 49 kDa in size by peptide mass and has 8 predicted N-glycosylation sites (note, not all sites will be expected to be glycosylated).

One goal was to develop a microchip capillary electrophoresis-based method to characterize and monitor low molecular weight (LMW) fragments of a heavily glycosylated, sialic acid containing protein (e.g., Protein 1) for research stability studies and for quality control (QC) studies.

Characteristics of Protein 1 are shown in Table 9 below:

TABLE 9

| Protein 1 Molecular Properties | |
|---|---|
| Molecular Weight without glycans (Intact MS) | 49 kDa |
| Molecular Weight with glycans (SEC-MALS) | 64 kDa |
| Predicted N-linked glycosylation sites | 8 |

Abbreviations: Intact MS, intact protein mass spectrometry; SEC-MALS, size exclusion chromatography multiple angle laser light scattering.

Figure 2:
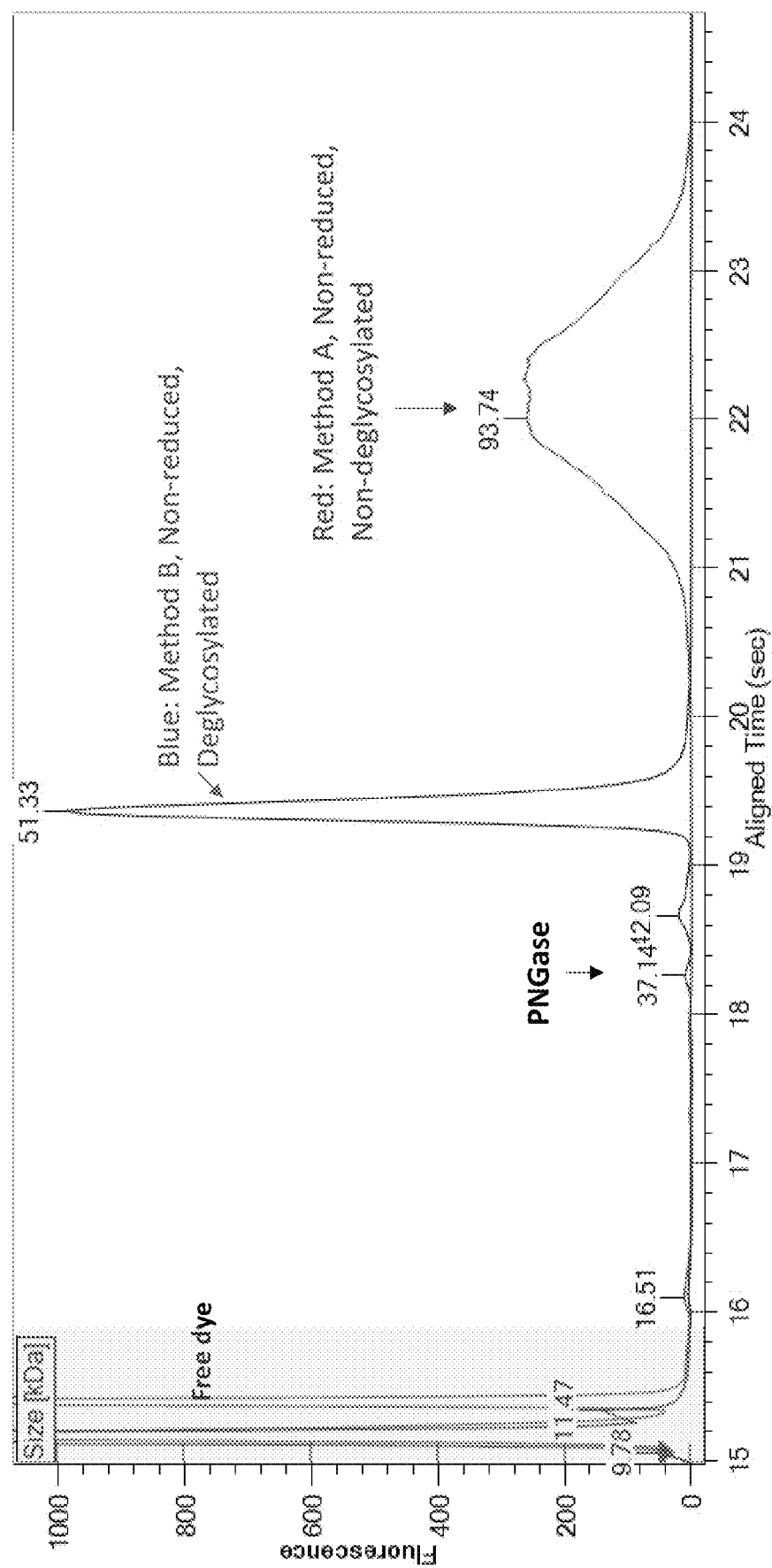
FIG. 2 is an electropherogram generated using Protein 1 under non-reduced conditions, using a protocol without deglycosylation (Method A, shown in red), and a protocol with deglycosylation prior protein labeling (Method B, shown in blue). The numeric peak labels indicate the molecular weight of the proteins as measured by microchip capillary electrophoresis (MCE). The Rapid PNGase F (PNGase) peak appears in the electropherogram where indicated.
Figure 4:
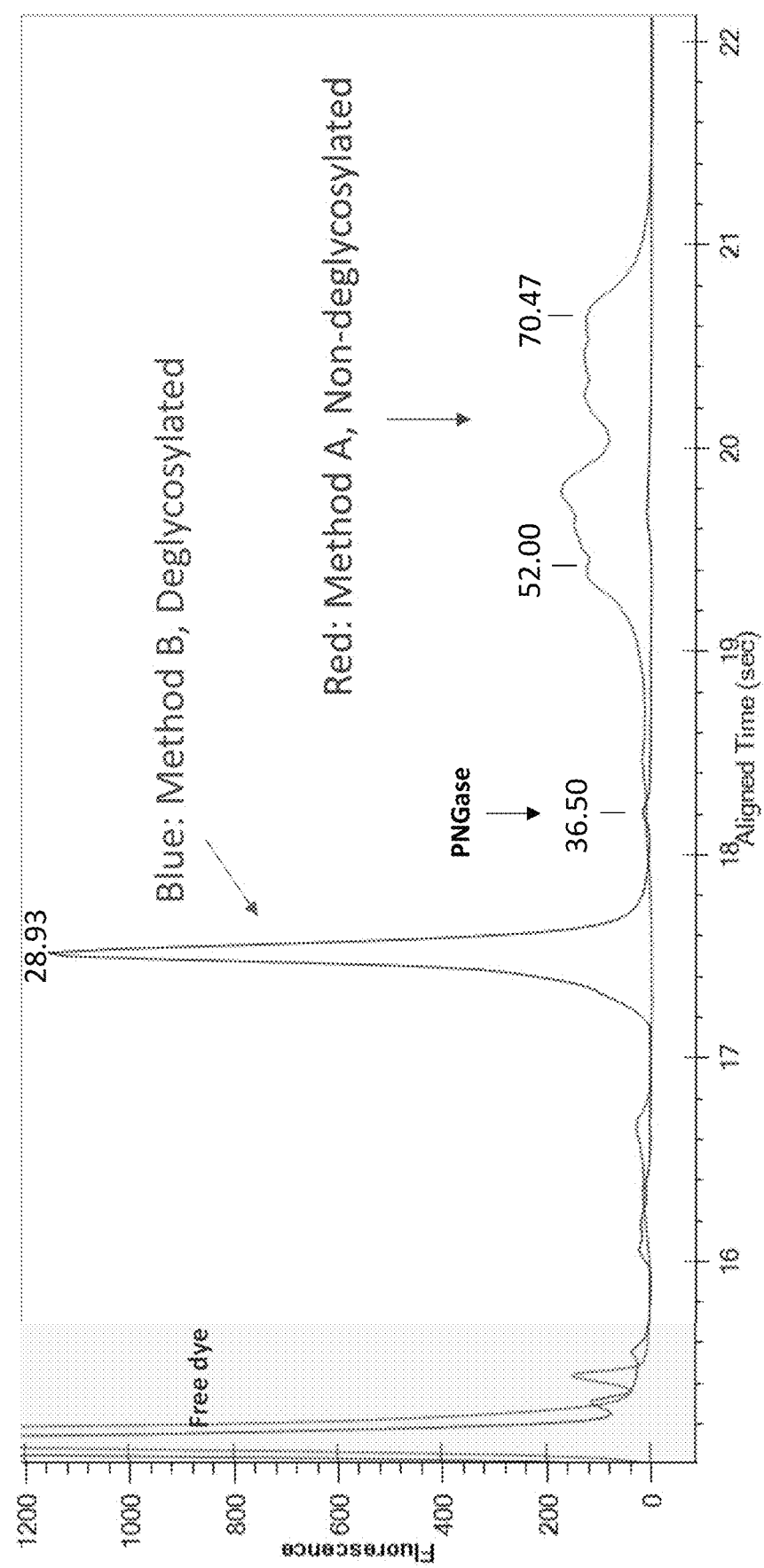
FIG. 4 is an electropherogram generated using Protein 1 under reducing conditions, using a protocol without deglycosylation (Method A, shown in red), and a protocol with deglycosylation before protein labeling (Method B, shown in blue). The numeric peak labels indicate the molecular weight of the proteins as measured by MCE. The PNGase F peak appears in the method B electropherogram, as indicated. The gray shaded box indicates free dye peaks.

A comparison of a protocol without deglycosylation (Method A, Example 2) and a protocol with deglycosylation prior to labeling (Method B, Example 3) is shown in FIG. 1. A comparison of the electropherograms of Protein 1 produced by Method A and Method B is shown in FIG. 2 for non-reduced (NR) conditions, and in FIG. 4 for reduced (R), respectively. For NR conditions, as a result of Method A (without deglycosylation), there was a broad peak in the electropherogram with no peak resolution (i.e., no separation of Main, high molecular weight (HMW) and low molecular weight (LMW) peaks). In addition, the peak position appeared at a much higher molecular weight (MW) region (70-120 kDa) than what was expected at about 64 kDa based on an orthogonal method. The MCE assay can inaccurately estimate size with a larger error when the protein is glycosylated (described by Engel et al. in Electrophoresis, 2015 August; 36(15):1754-8). In addition, there was free dye peak interference at <20 kDa that may mask any LMW peaks below 20 kDa.

Figure 3:
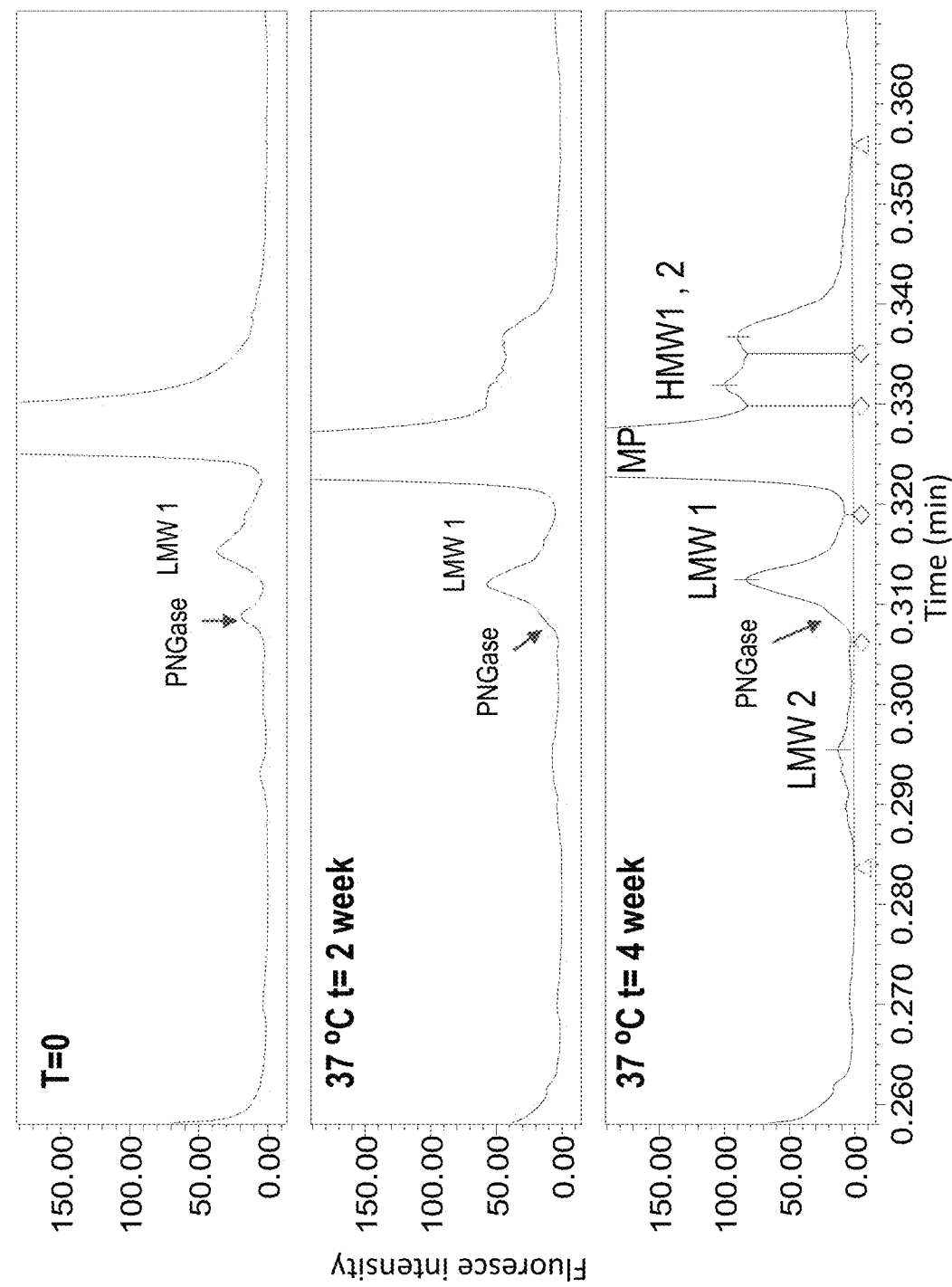
FIG. 3 shows three electropherograms generated using Protein 1 under non-reduced conditions using Method B (deglycosylation prior to labeling). Protein 1 samples were treated with thermal stress prior to analysis at 37° C. for no time (0, red, top), 2 weeks (blue, middle), or 4 weeks (black, bottom). The low molecular weight 1 peak (LMW 1) peak increased with stress, and merged with PNGase peak.

In contrast, as result of Method B, where deglycosylation occurs prior to labeling (Example 3), there is peak resolution and baseline separation between peaks (Main, HMW, LMW peaks). The Main peak appeared close to the expected MW (about 49 kDa). The protocol is stability indicating and more accurate with molecular sizing. However, Method B's protocol also requires 3 hours of deglycosylation, which limits the overall throughput of the assay. Moreover, the PNGase peak (about 36 kDa) interferes with the LMW 1 and 2 peaks (impurity peaks from fragments of Protein 1). Especially for thermally-stressed Protein 1 samples, the LMW 1 peak increases and broadens, merging with PNGase peak (FIG. 3). Another nearby artifact is the free dye peak interference at <20 kDa. The combination of these artifacts can lead to inaccurate integration when quantifying impurities and limits the assay's ability to be stability indicating.

Similar observations were found for reduced conditions (FIG. 4): deglycosylation of glycoproteins is required for accurate sizing, separation and resolution of Main, LMW, and HMW peaks.

Example 6: Deglycosylation after Protein Labeling Using a Heavily Glycosylated, Sialic Acid Containing Protein A comparison of a protocols with deglycosylation before labeling (Method B) and after labeling (Method C) is shown in FIG. 1.

To develop a protocol with deglycosylation after labeling, the deglycosylation reaction conditions were optimized, as non-complete removal of the glycosylated peak was initially observed with a 30-minute deglycosylation reaction. Temperature, time, concentration and buffer conditions were varied to determine optimal deglycosylation of Protein 1.

Optimization to remove the incompletely-deglycosylated peak in the NR electropherogram of Protein 1 produced several improvements to the protocol. These included using NEB Rapid™ PNGase F and performing the deglycosylation at an elevated temperature, 50° C. for 10 minutes (using conventional PNGase F needs 3 hours incubation at 37° C.), increasing the endoglycosidase concentration, and adding Glycoprotein Buffer from the NEB PNGase kit.

Figure 5:
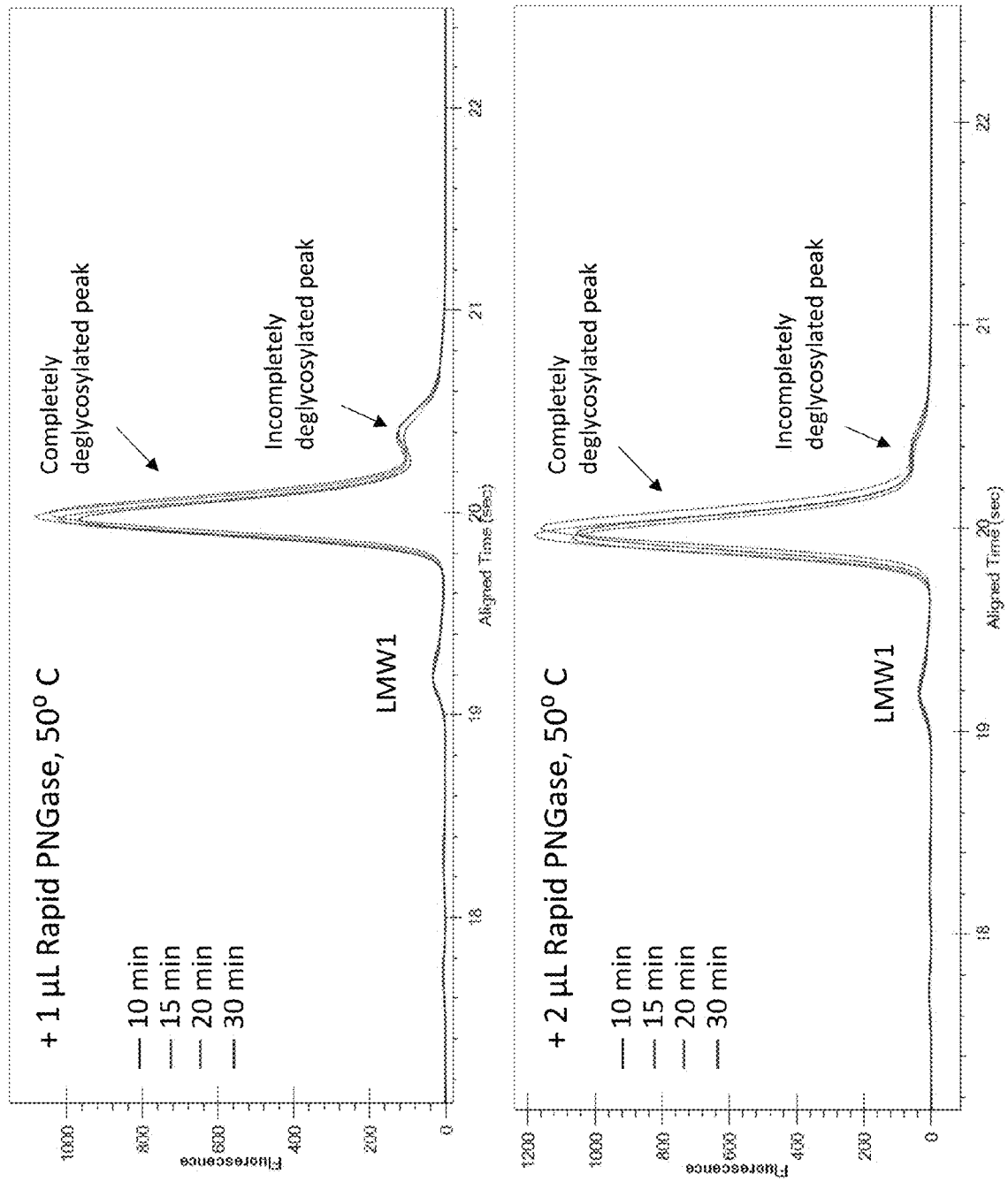
FIG. 5 is a pair of electropherograms generated with Protein 1, in which Protein 1 was deglycosylated after labeling (Method C). Top: the deglycosylation reaction was carried out with 1 µL Rapid™ PNGase, at 50° C., for 10, 15, 20 and 30 minutes. Bottom: the deglycosylation reaction was carried out with 2 µL Rapid™ PNGase, at 50° C., for 10, 15, 20 and 30 minutes.

Experiments showed increasing reaction time had no obvious improvement in deglycosylation. FIG. 5 shows electropherograms generated using Protein 1, with 1 µL or 2 µL Rapid™ PNGase F (non-reducing format, NEB P0711), at 50° C., with reaction times varying from 10 to 30 minutes. As can be seen from FIG. 5, there was no obvious improvement (i.e. reduction of the incompletely deglycosylated peak) with reaction times of more than 10 minutes.

Figure 6:
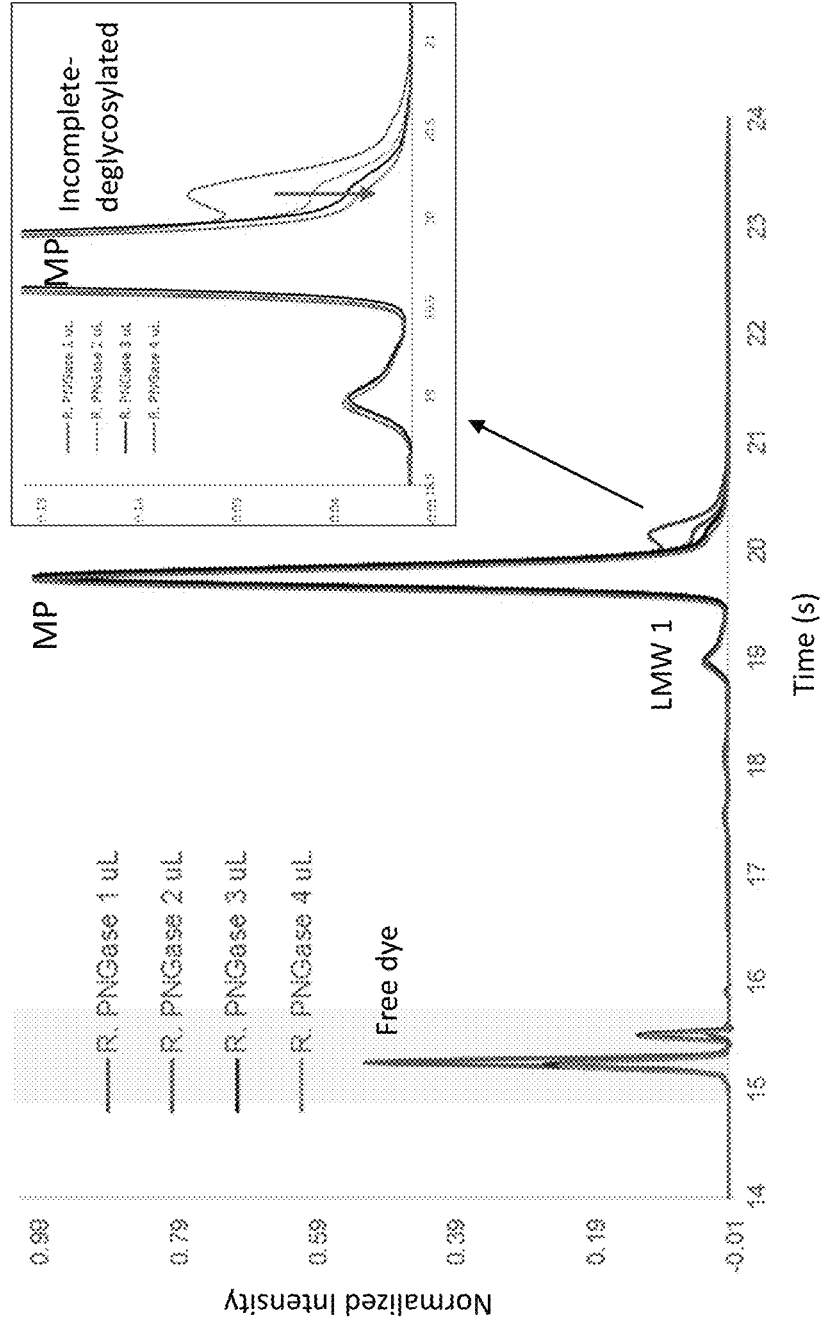
FIG. 6 is an electropherogram generated using Method C and Protein 1, showing the results of deglycosylation with 1, 2, 3, or 4 µL of Rapid™ PNGase F in a reaction held at 50° C., for 10 minutes. Inset shows the Protein 1 incompletely deglycosylated peak (right hand shoulder to the main peak), with the arrow indicating a reduction in glycosylated protein with increased amounts of Rapid™ PNGase. Free dye peaks are indicated by the gray shaded box. MP, main peak; LMW 1, low molecular weight 1 peak.
Figure 7:
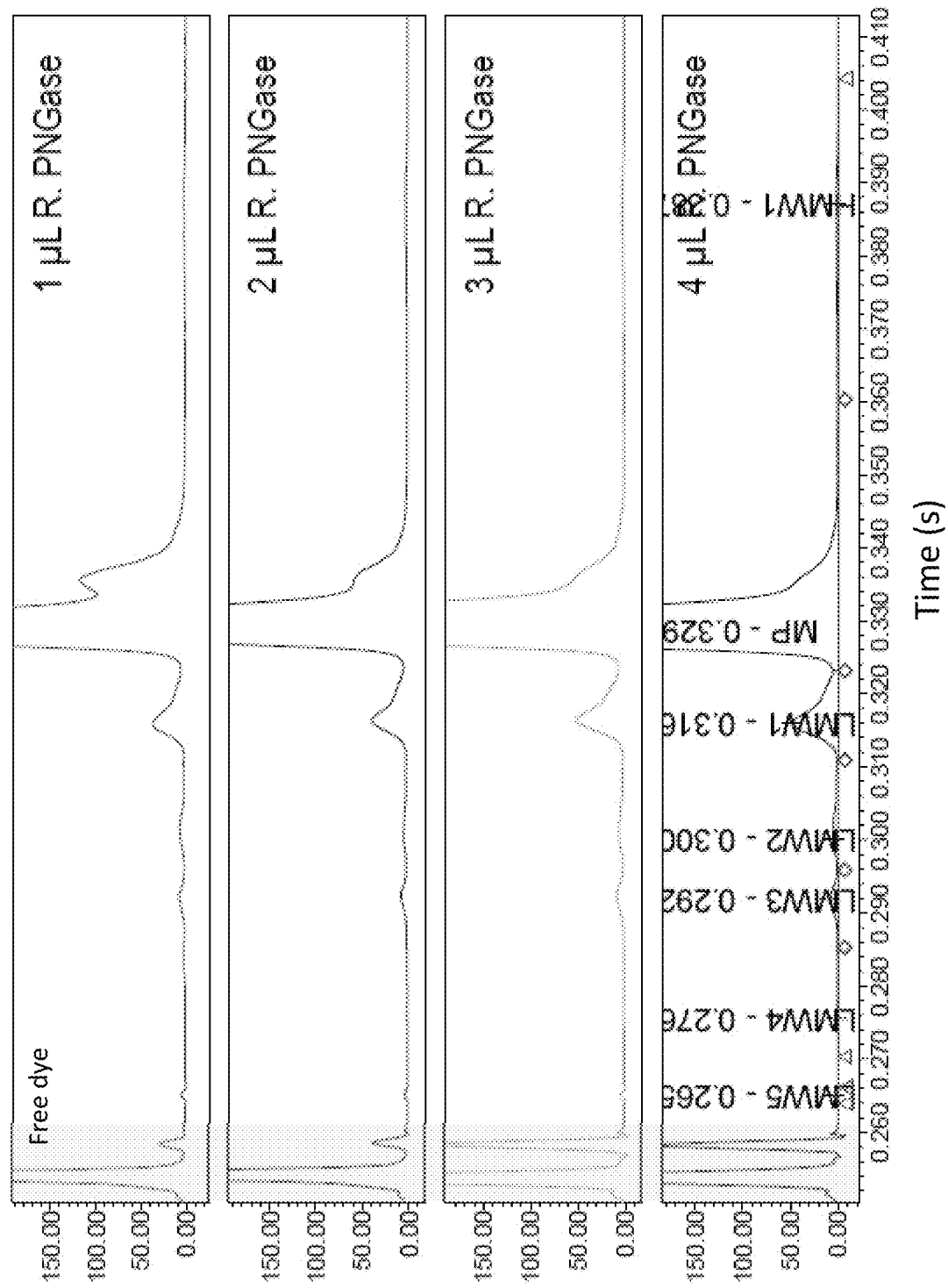
FIG. 7 is a series of four electropherograms generated using Method C (deglycosylation after labeling) and Protein 1, which was deglycosylated with 1, 2, 3, or 4 of Rapid™ PNGase (from top to bottom). Low molecular weight (LMW) peaks 1-5, main peak (MP), and high molecular weight peak (HMW) are indicated.

Increasing Rapid™ PNGase F concentration improved deglycosylation. Using the protocol for deglycosylation after labeling, 1, 2, 3 or 4 µL of Rapid™ PNGase F were added to the deglycosylation reaction, and the reaction was allowed to proceed at 50° C. for 10 minutes. The results are shown in FIG. 6 and FIG. 7. As can be seen in the inset of FIG. 6, increasing the concentration of Rapid™ PNGase F decreases the Protein 1's incomplete-deglycosylation shoulder peak.

Adding 1-4 µL of Rapid™ PNGase F provided robust results. Electropherograms generated using Reference Protein 1 deglycosylated using 1, 2, 3 or 4 µL of Rapid™ PNGase F are shown in FIG. 7. Area under the indicated peaks was integrated using Empower, and the results are provided in Table 10 below.

TABLE 10

Integration of Protein 1 peaks generated using different amounts of Rapid™ PNGase F

| Rapid™ PNGase | LMW2-5 | LMW 1 | MP | HMW |
|---|---|---|---|---|
| 1 µL | 2.27 | 4.09 | 93.01 | 0.62 |
| 2 µL | 1.94 | 4.23 | 93.24 | 0.60 |
| 3 µL | 1.71 | 4.05 | 93.75 | 0.50 |
| 4 µL | 1.78 | 4.10 | 93.38 | 0.75 |
| % RSD | 12.95 | 1.90 | 0.33 | 16.64 |

% RSD stands for percent relative standard deviation.

Integration results showed that although there was a decreasing shoulder peak post main peak (incompletely deglycosylated Protein 1) that was observed with a higher Rapid™ PNGase F concentration, the total percentage of integration of the main peak (MP) had the highest value at around 3 µL. From 1 µL to 4 µL of PNGase, the % RSD for the MP was 0.33%, suggesting that using Rapid™ PNGase F concentrations of 1-4 µL per reaction provide robust results. Following this trend, using more Rapid™ PNGase is expected to provide similar results.

Figure 8:
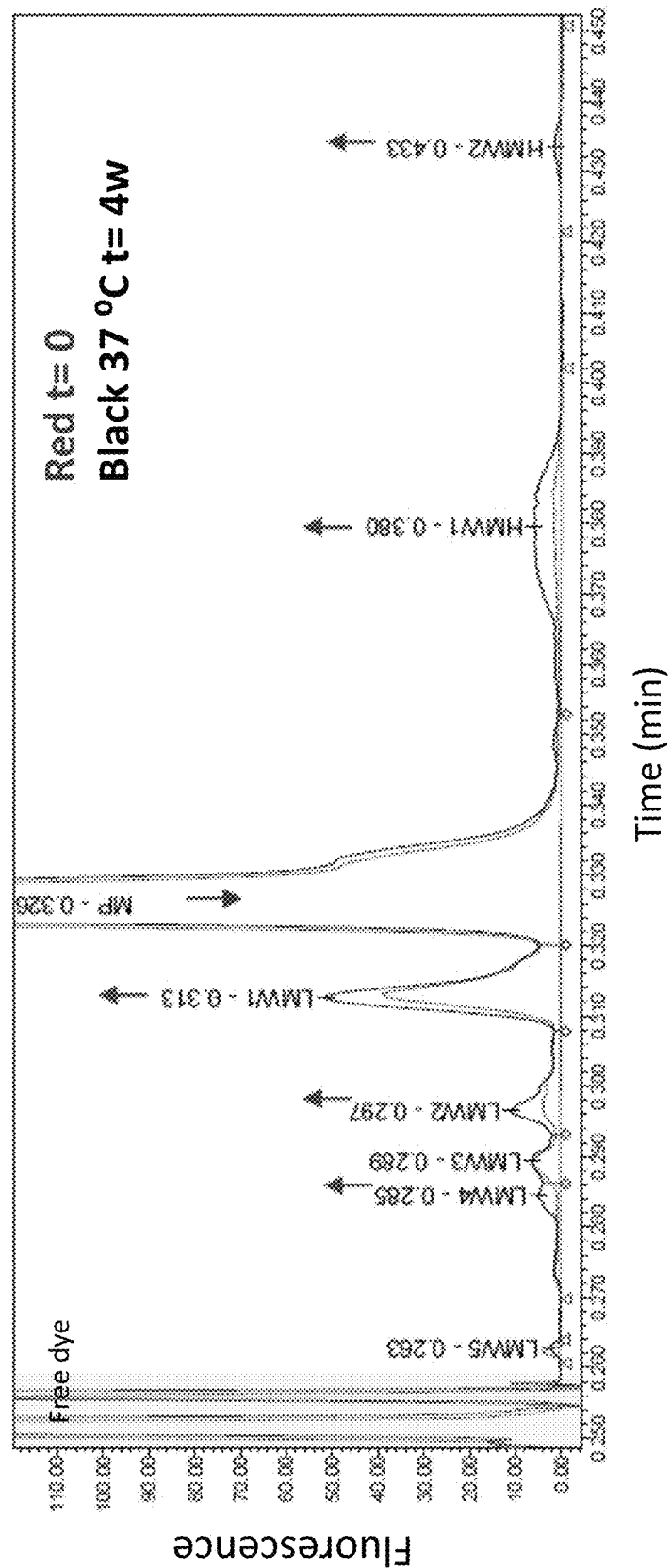
FIG. 8 is an electropherogram generated from Method C (deglycosylation after labeling) using Protein 1 that was thermally stressed by holding the protein at 37° C. for 4 weeks (37 C 4 w, Black) and non-stressed Protein 1 (t=0, Red). Deglycosylation was carried out using Rapid™ PNGase F.

Method C, where deglycosylation occurs after labeling, enables this MCE assay to be both precise and stability indicating. Protein 1 was stressed by holding the protein solution at 37° C. for 4 weeks (stressed Reference Standard, or "SRS", "37° C. 4 w" in Tables 11 and 12, compared to "RS" or non-stressed Reference Standard), and assayed using the deglycosylation following labeling protocol and MCE described here. This stressed Protein 1 was compared to non-stressed Protein 1 (time equal to 0, or t0, i.e. no 37° C. hold). Electropherograms were generated for stressed and non-stressed Protein 1 (FIG. 8), and indicated peaks were integrated using Empower. Measurements were repeated for three replicates (S1-S3), and the results are shown in Tables 11 and 12 below.

TABLE 11

Comparison of Stressed (SRS) and Non-Stressed (RS) Protein 1 using a deglycosylation after labeling protocol

| Stress | | LMW5 (%) | LMW4 (%) | LMW3 (%) | LMW2 (%) | LMW1 (%) | MP (%) | HMW1 (%) | HMW2 (%) |
|---|---|---|---|---|---|---|---|---|---|
| RS (t0) | S1 | 0.11 | 0.20 | 0.75 | 0.81 | 4.22 | 93.36 | 0.54 | — |
| | S2 | 0.07 | 0.17 | 0.70 | 0.80 | 4.22 | 93.57 | 0.48 | — |
| | S3 | 0.12 | 0.17 | 0.73 | 0.81 | 4.21 | 93.38 | 0.57 | — |
| SRS (37° C., 4 w) | S1 | 0.08 | 0.64 | 0.71 | 1.37 | 5.46 | 89.25 | 2.34 | 0.15 |
| | S2 | 0.10 | 0.63 | 0.71 | 1.39 | 5.52 | 89.25 | 2.19 | 0.20 |
| | S3 | 0.16 | 0.68 | 0.68 | 1.35 | 5.45 | 89.63 | 1.87 | 0.18 |

TABLE 12

Percent Relative Standard Deviation (% RSD) of Stressed and Non-Stressed Protein 1 (N = 3)

| | | LMW (%) | MP (%) | HMW (%) |
|---|---|---|---|---|
| RS (t0) | Average | 6.03 | 93.36 | 0.54 |
| | % RSD | 1.20 | 0.10 | 8.6 |
| SRS (37° C., 4 w) | Average | 8.31 | 89.38 | 2.31 |
| | % RSD | 0.55 | 0.25 | 9.98 |
| | Difference | 2.28 | −4.1 | 1.8 |

Three repeated measurements of RS and SRS showed multiple LMW and HMW peaks were consistently identified between runs and integrated with less than 1% RSD for LMW and MP peak. All the changes were significant from RS to SRS. A comparison of electropherograms from stressed, and non-stressed Protein 1 prepared by Method C (FIG. 8) indicated that this method is precise and stability indicating.

When deglycosylation with PNGase F is performed before dye labeling (Method B), the PNGase F peak is visible in the electropherogram profile and interferes with the LMW 1 and LMW 2 peak. A long deglycosylation time (3 hours) is used, and there is free dye interference (<20 kDa).

When deglycosylation with Rapid™ PNGase F is performed after labeling with dye (Method C), no PNGase peak is visible in the electropherogram. There is fast and complete deglycosylation (e.g., in 10 minutes). Resolution of MP, HMW and LMW peaks is achieved along with minimal free dye interference down to about 10 kDa region (e.g. in FIG. 8, LMW 5 peak is 11 kDa and is baseline resolved from the free dye peak artifact).

In summary, MCE methods using deglycosylation after dye labeling, such as Method C, have good resolution, are stability indicating, high throughput, reproducible, and avoids assay artifacts from PNGase F Peak interference and free dye interference. The methods also show good precision, linearity, and robustness. These assays can be used in a plate-based high throughput format which is suitable for quality control purposes.

Example 7: Comparison of MCE Results Generated with and without Deglycosylation Using Protein 2

Protein 2 is a single chain recombinant (Fab')2-like protein comprising a single chain fusion protein that includes a ligand binding domain linked by a linker of sequence GGGGSGGGGSGGGGSGGGGSGGGGSGGGGS (SEQ ID NO: 1). The protein has a predicted molecular weight of 48 kDa (peptide backbone). Protein 2 has 8 N-glycosylation sites.

Figure 9:
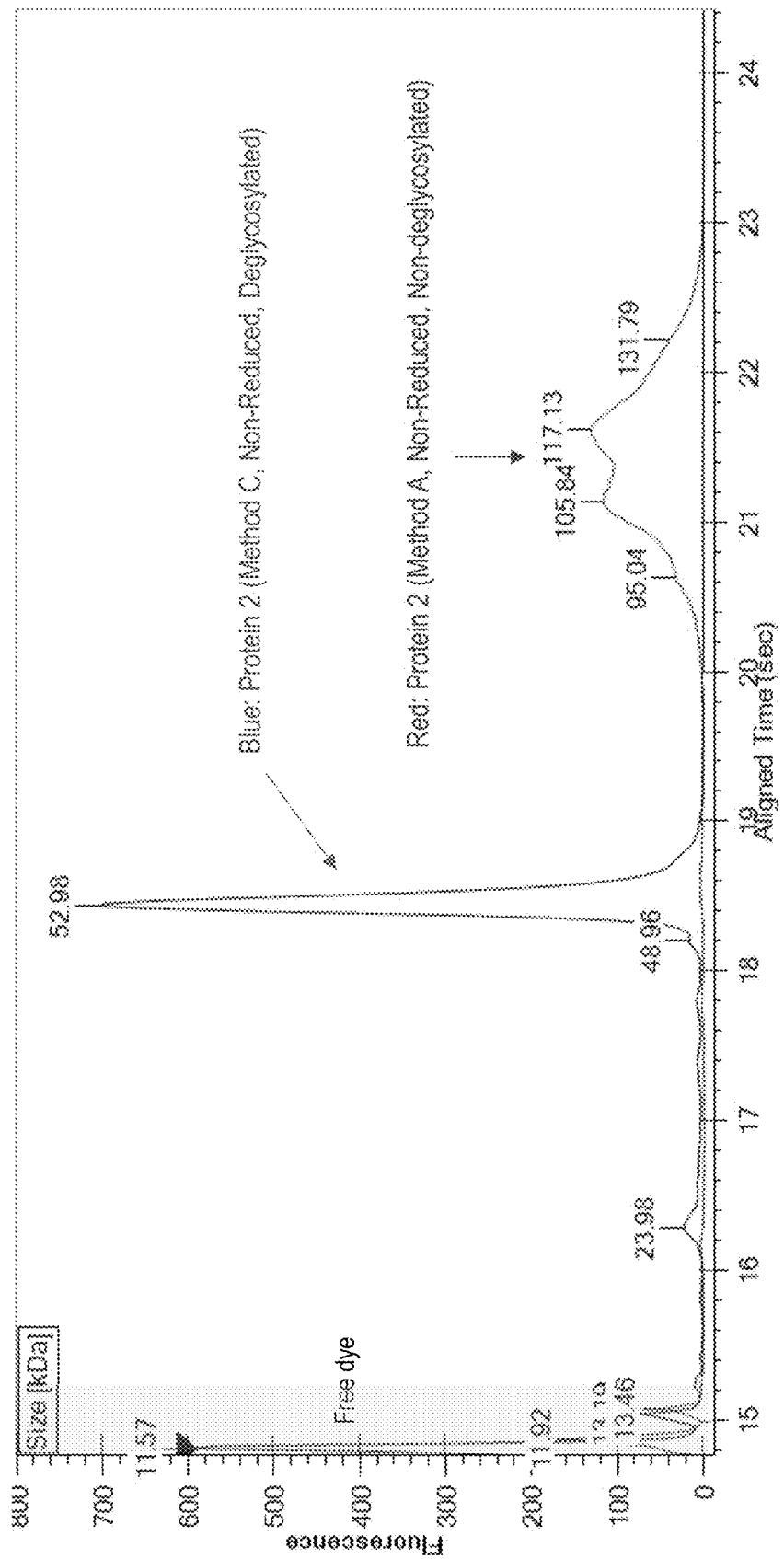
FIG. 9 is an electropherogram generated using Protein 2, which compares Protein 2 labeled with deglycosylation (Method C) and without deglycosylation (Method A), under non-reduced conditions. PNGase F has an expected size of 37 KDa, and this peak is not present. Free dye peaks are indicated by the shaded box.

MCE electropherograms for Protein 2 were generated using a protocol without deglycosylation (Method A, Example 2), and with deglycosylation after labeling (Method C, Example 4), under both non-reduced and reduced conditions. As can be seen in FIG. 9, without deglycosylation, there was only a broad peak without separation appearing at a MW region (90-140 kDa) which was much larger than theoretical value (about 48 kDa). To the contrary, deglycosylation produced a main peak near the expected MW (48 kDa) and clearly resolved LMW peaks. Moreover, a PNGase peak (~36 kDa) did not appear in the electropherogram.

Example 8: Comparison of MCE Results Generated with and without Deglycosylation Using Protein 3

Protein 3 is a recombinant human IgG 1 Fc subunit cleaved at a specific site by a recombinant cysteine protease. The protein has a predicted molecular weight of 23 kDa. The protein has one N-glycosylation site.

Figure 10:
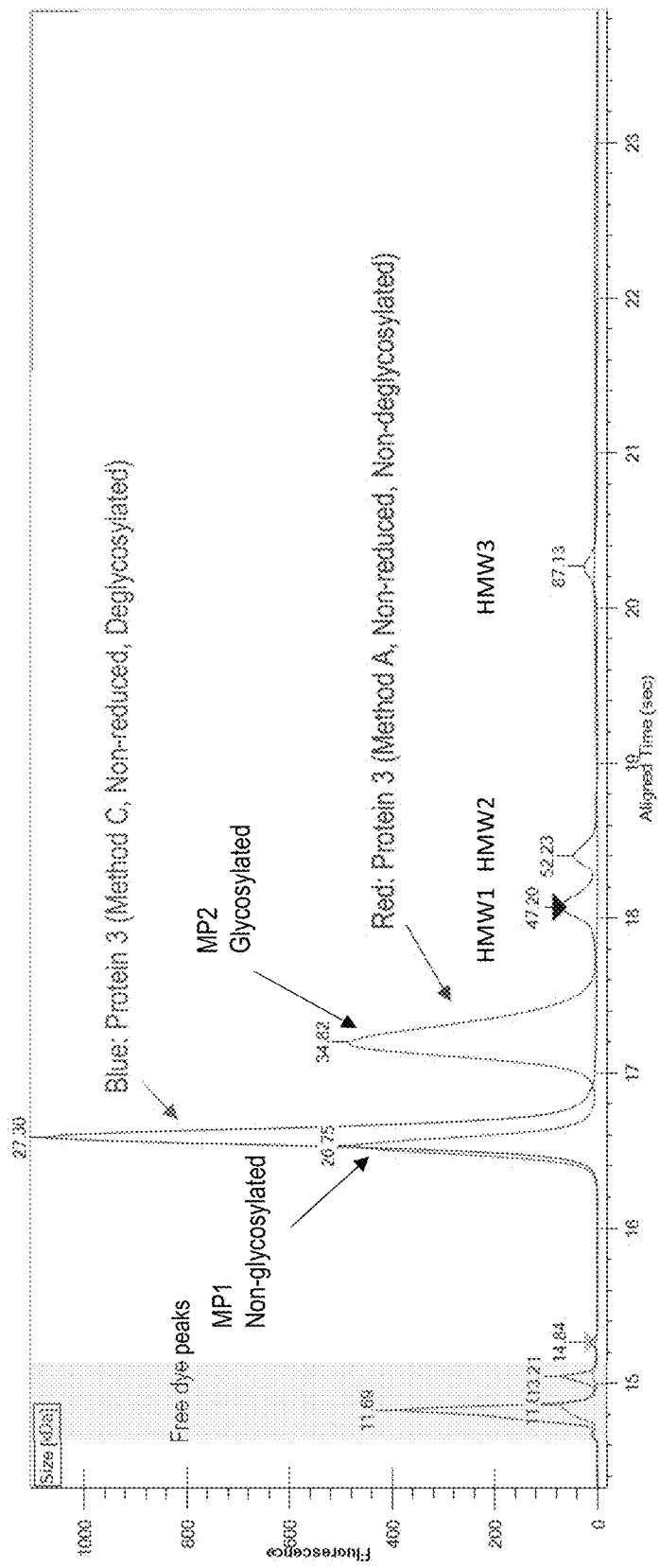
FIG. 10 is an electropherogram generated using Protein 3, which compares Protein 3 treated with deglycosylation after labeling (blue, Method C) and without deglycosylation treatment (red, Method A), under non-reduced conditions. The numeric peak labels indicate the molecular weight of proteins and protein fragments measured by MCE.
Figure 11:
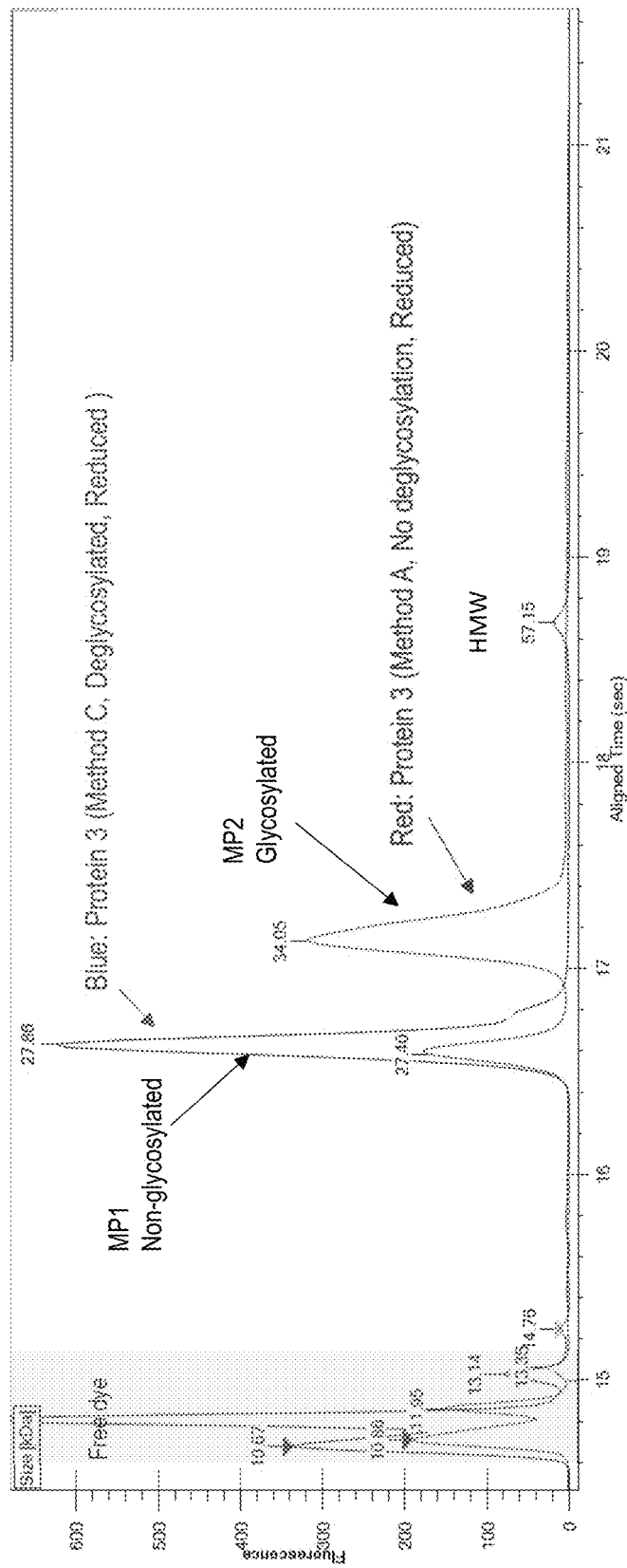
FIG. 11 is an electropherogram comparing Protein 3, which was treated with deglycosylation after labeling (blue, Method C) and without deglycosylation (red, Method A), under reduced conditions. The numeric peak labels indicate the molecular weight of proteins and protein fragments measured by MCE.

MCE electropherograms were generated using a protocol without deglycosylation (Method A, Example 2), and with deglycosylation after labeling (Method C, Example 4), under non-reduced conditions. The results can be seen in FIG. 10. In the non-deglycosylation profile, two main peaks (MPs) were found that represent non-glycosylated population (MP1, left) and glycosylated population (MP 2, right) in the original sample. In the deglycosylated profile, only the non-glycosylated peak was observed and several HMW peaks were resolved. The same comparison was also performed under reducing conditions (FIG. 11).

Example 9: Stability Assessment of a Monoclonal Antibody

Protein 4 is a human IgG4-based monoclonal antibody with a molecular weight of 145 kDa and 2 N-linked glycosylation sites.

Figure 12:
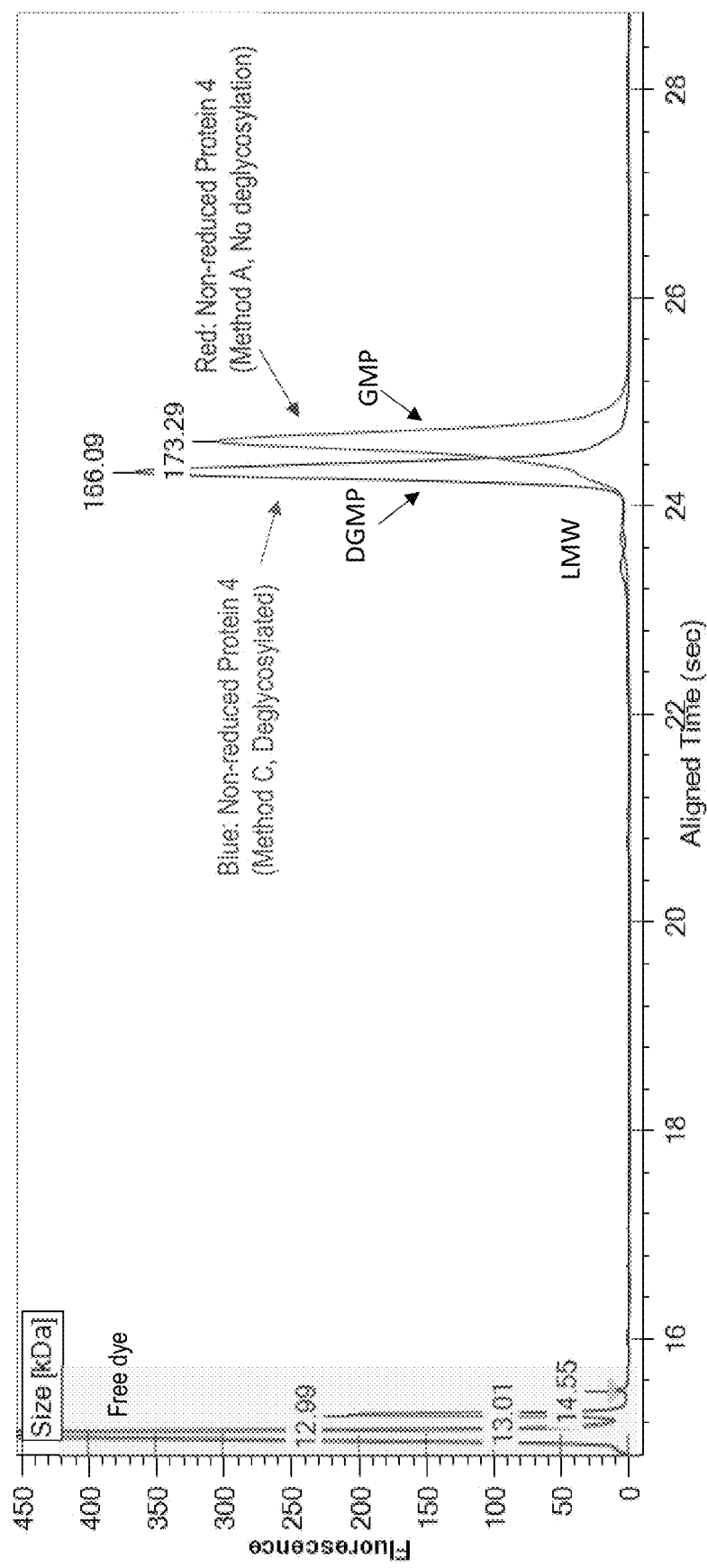
FIG. 12 is an electropherogram comparing Protein 4 without deglycosylation (Method A, red) and deglycosylated after labeling (Method C, blue). Protein 4 was denatured using non-reducing (NR) conditions. The numeric peak labels indicate the molecular weight measured by MCE. LMW: low molecular weight; DGMP: Deglycosylated Main Peak; GMP: Glycosylated Main Peak. Free dye peaks are indicated by the shaded box.
Figure 13:
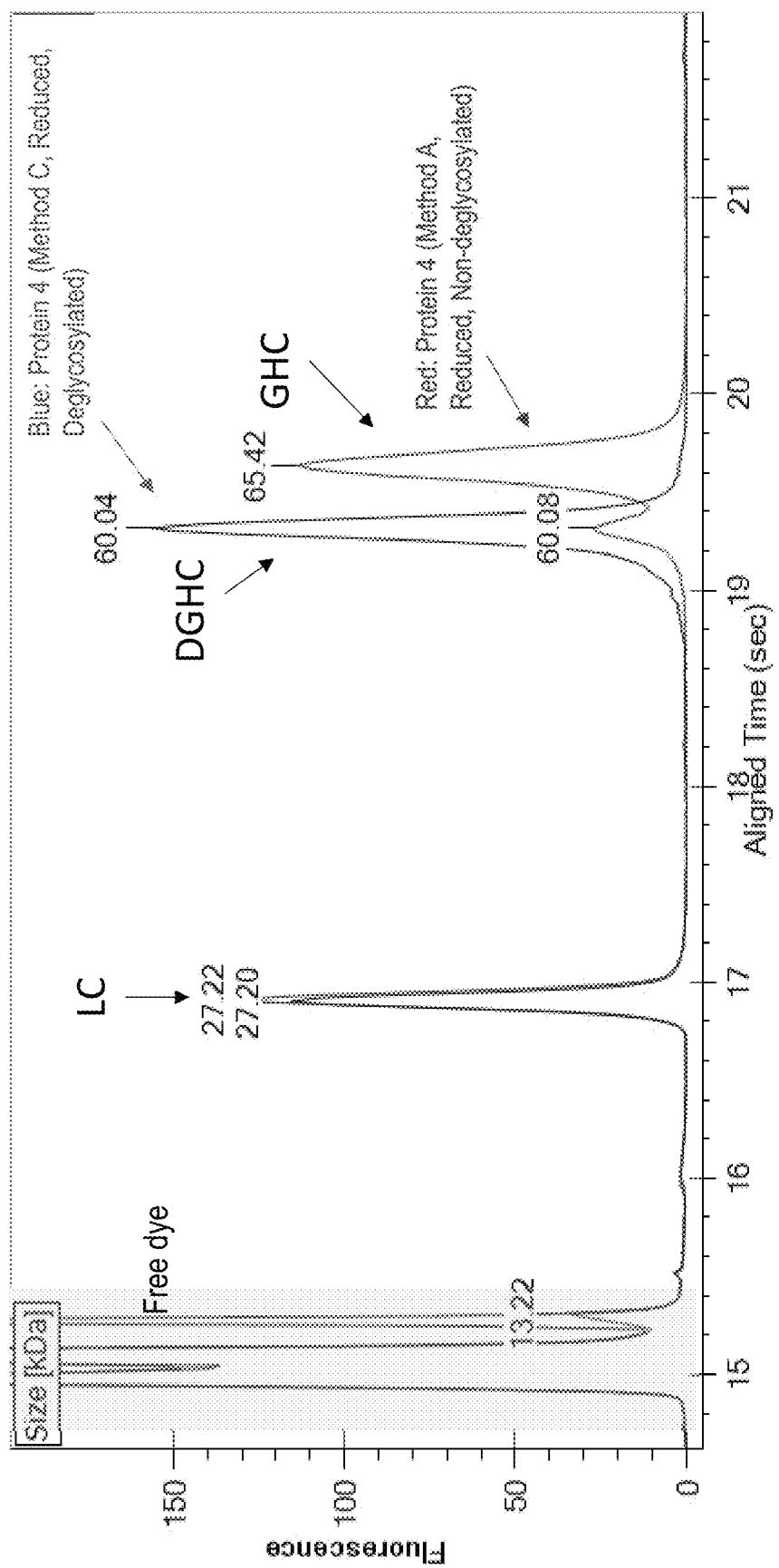
FIG. 13 is an electropherogram comparing Protein 4 labeled without deglycosylation (Method A, red) and deglycosylated after labeling (Method C, blue). Protein 4 was denatured using reducing (R) conditions. LC: Light Chain; DHC: Deglycosylated Heavy Chain; GHC: Glycosylated Heavy Chain. Free dye peaks are indicated by the shaded box.

MCE electropherograms were generated for Protein 4 samples prepared using a protocol without deglycosylation (Method A, in FIGS. 12 and 13), and using a protocol with deglycosylation after labeling (Method C, in FIGS. 12 and 13). The protein was assayed using denaturation under both non-reducing conditions (FIG. 12) and reducing conditions (FIG. 13). As can be seen in FIG. 13, deglycosylation shifts the Glycosylated Main Peak (GMP) to a Deglycosylated Main Peak (DGMP) at a lower molecular weight as the result of the removal of glycans. In FIG. 13, deglycosylation reduces the size of the Heavy Chain (HC) peak, as can be seen by comparing the Deglycosylated Heavy Chain (DGHC) and Glycosylated Heavy Chain (FGHC) peaks.

Example 10: Stability Assessment of Photo-Stressed Protein 1

Figure 14:
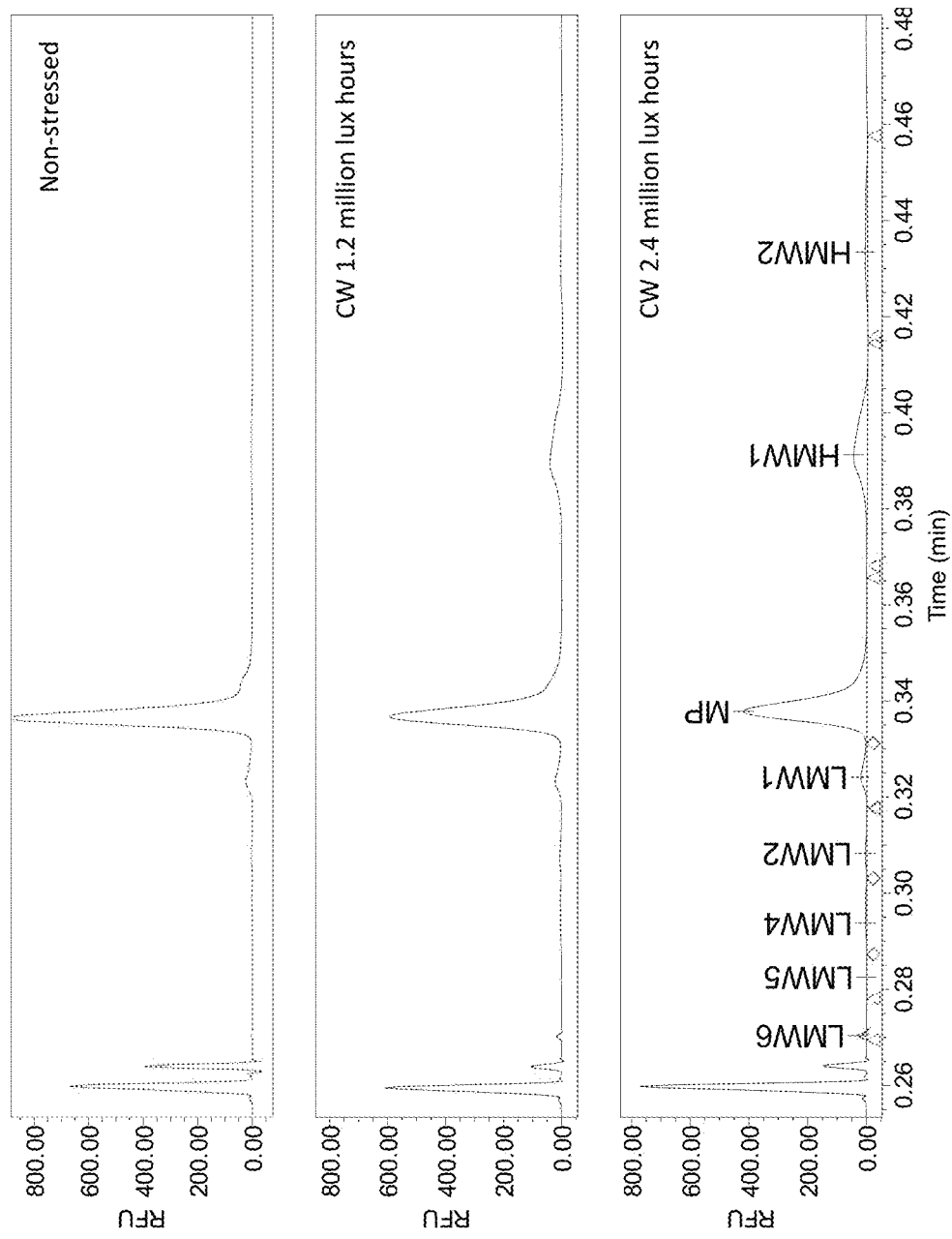
FIG. 14 shows three electropherograms assaying the effect of photo-stress on protein stability that were generated under non-reduced conditions, using Method C and Protein 1. Protein 1 was photo-stressed under cool white (CW) fluorescent lamp light with 1.2 million lux hours (MLH) accumulative exposure (blue, middle), and 2.4 MLH accumulative exposure (black, bottom), and compared to non-stressed Protein 1 (red, top). Deglycosylation was carried out using Rapid™ PNGase F. LMW: low molecular weight; MP: main peak; HMW: high molecular weight.
Figure 15:
FIG. 15 shows three electropherograms assaying the effect of photo-stress on protein stability that were generated under non-reduced conditions, using Method C and Protein 1. Protein 1 was photo-stressed under integrated near ultraviolet (UVA) energy of 200 watt hours/square meter (blue, middle), and 400 watt hours/square meter (black, bottom), and compared to non-stressed Protein 1 (red, top). Deglycosylation was carried out using Rapid™ PNGase F.LMW: low molecular weight; MP: main peak; HMW: high molecular weight.

Protein 1 was photo-stressed by exposing the protein solution under cool white (CW) fluorescent lamp light with 1.2 and 2.4 million lux hours (MLH) accumulative exposure (FIG. 14), or under integrated near ultraviolet (UVA) with an energy of 200 and 400 watt hours/square meter (FIG. 15). Samples were assayed using the deglycosylation following labeling protocol (Method C) and MCE as described in Examples 1 and 4. Stressed Protein 1 samples were compared to non-stressed Protein 1 control (which was incubated under the same conditions but covered with aluminum foil). Electropherograms were generated for stressed and non-stressed Protein 1, and indicated peaks were integrated using Empower. The results are shown in Table 13. Both CW and UVA exposure led to slightly increases of LMW peaks and significant increases of HMW peaks, which may due to photo-initiated formation of covalent-bonded dimers and multimers. The results show that this method is stability indicating and able to evaluate the fragmentation and covalent-bonded HMW formation of protein under stress conditions.

TABLE. 14

Comparison of photo stressed and non-stressed protein 1 using a deglycosylation after labeling protocol (Method C).

| Photo stress conditions | LMW (%) | MP (%) | HMW (%) |
|---|---|---|---|
| Non-stressed | 5.01 | 93.61 | 1.38 |
| CW 1.2 million lux hours | 6.61 | 77.27 | 16.12 |
| CW 2.4 million lux hours | 7.54 | 69.96 | 22.50 |
| UVA 200 watt hours/m$^2$ | 6.48 | 84.92 | 8.60 |

What is claimed is:

1. A method of analyzing a sample comprising a protein of interest, the method comprising:
   a. denaturing the sample;
   b. labeling the denatured sample with a fluorescent label to produce a labeled sample;
   c. quenching un-reacted fluorescent label in the labeled sample;
   d. deglycosylating the labeled sample with an endoglycosidase; and
   e. performing electrophoresis on the labeled sample after deglycosylating;
   wherein the sample is denatured, labeled and quenched in steps (a) through (c) prior to deglycosylation in step (d).

2. The method of claim 1, wherein the protein of interest comprises at least one glycosylation site.

3. The method of claim 1, wherein the protein of interest is a glycosylated protein.

4. The method of claim 1, wherein the protein of interest comprises an antigen binding domain.

5. The method of claim 4, wherein the protein of interest comprises an antibody, an antibody fragment or an scFv.

6. The method of claim 1, wherein the protein of interest comprises an Fc domain.

7. The method of claim 1, wherein the protein of interest comprises a receptor fusion protein.

8. The method of claim 7, wherein the receptor fusion protein is a receptor-Fc-fusion protein or a soluble TCR-Fc fusion protein.

9. The method of claim 1, wherein the protein of interest is a recombinant human protein.

10. The method of claim 1, wherein the protein of interest comprises at least one attached glycan that is N-linked.

11. The method of claim 1, wherein the endoglycosidase catalyzes deglycosylation of N-linked glycans.

12. The method of claim 11, wherein the endoglycosidase is selected from the group consisting of Peptide-N-Glycosidase F (PNGase F), Endoglycosidase H (Endo H), Endoglycosidase S (Endo S), Endoglycosidase D, Endoglycosidase F1, Endoglycosidase F2 and Endoglycosidase F4.

13. The method of claim 11, wherein the endoglycosidase is PNGase F.

14. The method of claim 13, wherein the PNGase F is Rapid PNGase F.

15. The method of claim 14, wherein the Rapid PNGase F is non-reducing.

16. The method of claim 13, wherein deglycosylating the labeled sample comprises heating the sample to about 50° C. for 10 minutes.

17. The method of claim 16, wherein deglycosylating the labeled sample comprises a reaction mixture comprising between 0.2-1.5 mg labeled protein of interest, and between 1-5 μL Rapid PNGase F in a 10 μL reaction volume, excluding the volume of the Rapid PNGase F.

18. The method of claim 1, wherein the protein of interest comprises at least one glycan that is an O-linked glycan.

19. The method of claim 18, wherein the endoglycosidase catalyzes deglycosylation of O-linked glycans.

20. The method of claim 19, wherein the endoglycosidase comprises Endo-α-N acetylgalactosaminidase (O-glycosidase).

21. The method of claim 1, wherein labeling the denatured sample with the fluorescent label comprises heating the sample to about 35° C. for 10-30 minutes.

22. The method of claim 1, wherein the sample is denatured using a reducing solution.

23. The method of claim 22, wherein the reducing solution comprises dithiothreitol (DTT).

24. The method of claim 1, wherein the sample is denatured using a non-reducing solution.

25. The method of claim 24, wherein the non-reducing solution comprises iodoacetamide (IAM).

26. The method of claim 1, wherein denaturing the sample comprises heating the sample to between 40° C. and 99° C. for between 1 minute and 60 minutes.

27. The method of claim 1, wherein quenching the un-reacted fluorescent label comprises adding a stop solution.

28. The method of claim 1, further comprising analyzing a reference standard in parallel to the labeled sample after deglycosylating.

29. The method of claim 1, wherein the electrophoresis is selected from the group consisting of gel electrophoresis, isoelectric focusing, capillary electrophoresis (CE) or microchip capillary electrophoresis (MCE).

30. The method of claim 1, wherein the method results in reduced free dye interference in the less than 20 kDa range and a reduced or absent endoglycosidase peak in an electropherogram when compared to an electropherogram generated using a sample labeled after deglycosylation.

31. A method of determining stability of a protein of interest comprising:
   a. stressing a sample comprising the protein of interest;
   b. denaturing the stressed sample and a non-stressed sample comprising the protein of interest;
   c. labeling the stressed sample and the non-stressed sample with a fluorescent label to produce a labeled stressed sample and a labeled non-stressed sample;

d. quenching un-reacted fluorescent label in the labeled stressed sample and the labeled non-stressed sample;
e. deglycosylating the labeled stressed sample and the labeled non-stressed sample with an endoglycosidase;
f. performing microchip capillary electrophoresis (MCE) on the labeled stressed sample and the labeled non-stressed sample after deglycosylating to generate electropherograms for the stressed sample and the non-stressed sample; and
g. comparing the electropherograms from the stressed sample and the nonstressed sample after deglycosylating, thereby determining the stability of the protein of interest;
wherein the stressed sample and the non-stressed sample are denatured, labeled and quenched in steps (b) through (d) prior to deglycosylation in step (e).

* * * * *

SEQUENCE LISTING

<160> NUMBER OF SEQ ID NOS: 1

<210> SEQ ID NO 1
<211> LENGTH: 30
<212> TYPE: PRT
<213> ORGANISM: Artificial Sequence
<220> FEATURE:
<223> OTHER INFORMATION: linker

<400> SEQUENCE: 1

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```